United States Patent
Morrisey

(10) Patent No.: US 9,115,345 B2
(45) Date of Patent: Aug. 25, 2015

(54) MICRORNA INDUCTION OF PLURIPOTENTIAL STEM CELLS AND USES THEREOF

(75) Inventor: Edward E. Morrisey, Newtown Square, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/641,521

(22) PCT Filed: Mar. 25, 2011

(86) PCT No.: PCT/US2011/030012
§ 371 (c)(1),
(2), (4) Date: Oct. 16, 2012

(87) PCT Pub. No.: WO2011/133288
PCT Pub. Date: Oct. 27, 2011

(65) Prior Publication Data
US 2013/0035374 A1    Feb. 7, 2013

Related U.S. Application Data

(60) Provisional application No. 61/325,596, filed on Apr. 19, 2010.

(51) Int. Cl.
*C12N 15/00* (2006.01)
*C12N 5/02* (2006.01)
*C12N 5/074* (2010.01)

(52) U.S. Cl.
CPC ........ *C12N 5/0696* (2013.01); *C12N 2310/141* (2013.01); *C12N 2501/065* (2013.01); *C12N 2501/65* (2013.01)

(58) Field of Classification Search
CPC .................. C12N 2310/141; C12N 2501/065; C12N 2501/65
See application file for complete search history.

(56) References Cited

U.S. PATENT DOCUMENTS

| 4,873,316 A | 10/1989 | Meade et al. |
| 6,756,196 B2 | 6/2004 | Bertin |
| 2007/0269889 A1 | 11/2007 | Leake et al. |
| 2008/0280362 A1* | 11/2008 | Jaenisch et al. ............... 435/455 |
| 2009/0246875 A1 | 10/2009 | Yamanaka et al. |
| 2010/0062534 A1 | 3/2010 | Hochedlinger et al. |

FOREIGN PATENT DOCUMENTS

| EP | 264166 | 8/2006 |
| WO | WO/2009/091659 | 7/2009 |

OTHER PUBLICATIONS

Lin et al, "Mir-302 reprograms human skin cancer cells into a pluripotent ES-cell like state" (2008b) RNA 14: 2115-2124.
Pinkert et al., "An albumin enhancer located 10 kb upstream functions along with its promoter to direct efficient, liver-specific expression in transgenic mice", (1987) Genes Dev. 1:268-277.
Winoto and Baltimore, "A novel, inducible and T cell-specific enhancer located at the 3' end of the T cell receptor alpha locus", (1989) EMBO J. 8:729-733.
Byrne and Ruddle, "Multiplex gene regulation: a two-tiered approach to transgene regulation in transgenic mice", (1989) Proc. Natl. Acad. Sci. USA 86:5473-5477.
Camper and Tilghman, "Postnatal repression of the alpha-fetoprotein gene is enhancer independent", (1989) Genes Dev. 3:537-546.
Blelloch et al., "Generation of induced pluripotent stem cells in the absence of drug selection", Cell Stem Cell. 2007; 1:245-247.
Shu W, et al., "Wnt7b regulates mesenchymal proliferation and vascular development in the lung", Development. 2002; 129:4831-4842.
Cohen ED, et al. "Wnt signaling regulates smooth muscle precursor development in the mouse lung via a tenascin C/PDGFR pathway", J Clin Invest. 2009; 119:2538-2549.
Trivedi CM, et al., "Transgenic overexpression of Hdac3 in the heart produces increased postnatal cardiac myocyte proliferation but does not induce hypertrophy". J Biol Chem. 2008; 283:26484-26489.
Card DA, et al., "Oct4/Sox2-regulated miR-302 targets cyclin D1 in human embryonic stem cells", Mol Cell Biol. 2008; 28:6426-6438.
Lengner CJ, et al., "Oct4 expression is not required for mouse somatic stem cell self-renewal", Cell Stem Cell. 2007; 1:403-415.
Sommer CA, et al., "Induced pluripotent stem cell generation using a single lentiviral stem cell cassette", Stem Cells. 2009; 27:543-549.
Friedrich G, et al., "Promoter traps in embryonic stem cells: a genetic screen to identify and mutate developmental genes in mice", Genes Dev. 1991; 5:1513-1523.
Mali P, et al. "Butyrate greatly enhances derivation of human induced pluripotent stem cells by promoting epigenetic remodeling and the expression of pluripotency-associated genes", Stem Cells. 2010; 28:713-720.
Kramer et al. "The histone deacetylase inhibitor valproic acid selectively induces proteasomal degradation of HDAC2", EMBO J. 2003; 22:3411-3420.
Warren L, et al. "Highly efficient reprogramming to pluripotency and directed differentiation of human cells with synthetic modified mRNA", Cell Stem Cell. 2010; 7:618-630.
Lagarkova et al., "Induction of pluripotency in human endothelial cells resets epigenetic profile on genome scale", Cell Cycle. 2010; 9:937-946.
Seki et al., "Generation of induced pluripotent stem cells from human terminally differentiated circulating T cells", Cell Stem Cell. 2010; 7:11-14.
Takahashi et al., "Induction of pluripotent stem cells from mouse embryonic and adult fibroblast cultures by defined factors" Cell 126:663-76, 2006.
Suh et al., "Human embryonic stem cells express a unique set of microRNAs", 2004 (Dev. Biol. 270:488-498.
Drummond et al., (2005) "Clinical development of histone deacetylase inhibitors as anticancer agents", Annu Rev Pharmacol Toxicol 45: 495-528.
Calame et al., "Transcriptional controlling elements in the immunoglobulin and T cell receptor loci", (1988) Adv. Immunol. 43:235-275.
Banerji et al., "A lymphocyte-specific cellular enhancer is located downstream of the joining region in immunoglobulin heavy chain genes", (1983) Cell 33:729-740.
Queen et al., "Immunoglobulin gene transcription is activated by downstream sequence elements", (1983) Cell 33:741-748.

(Continued)

*Primary Examiner* — Brian Whiteman
(74) *Attorney, Agent, or Firm* — Mark S. Cohen; Pearl Cohen Zedek Latzer Baratz LLP

(57) ABSTRACT

Compositions and methods for inducing the formation of an induced pluripotential stem (iPS) cell from a somatic cell are disclosed. The compositions comprise miR 302-367 cluster and valproic acid. Further disclosed are methods for treatment of a disease or condition in a subject through the use of the compositions.

16 Claims, 21 Drawing Sheets

(56) References Cited

OTHER PUBLICATIONS

Edlund et al., "Cell-specific expression of the rat insulin gene: evidence for role of two distinct 5' flanking elements", (1985) Science 230:912-916.

Kessel et al., "Murine developmental control genes", (1990) Science 249:374-379.

Huangfu et al., "Induction of pluripotent stem cells by defined factors is greatly improved by small-molecule compounds", Nat Biotechnol. 2008a; 26:795-797.

Rosa et al., "The miR-430/427/302 family controls mesendodermal fate specification via species-specific target selection", Dev Cell. 2009; 16:517-527.

* cited by examiner

Figure 15
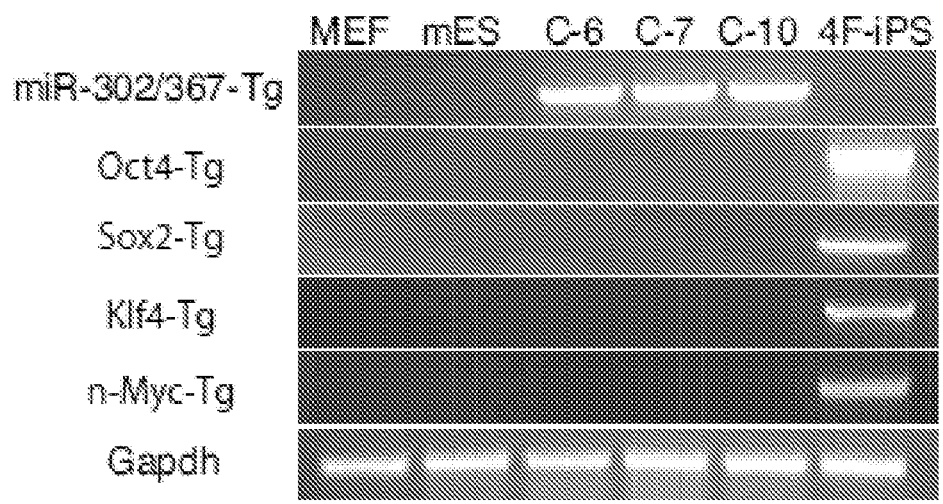
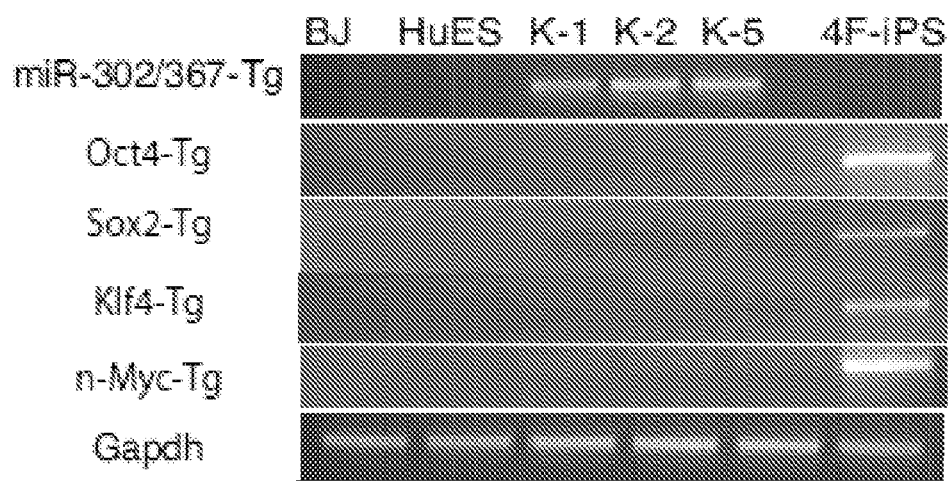

Figure 18

DNA fingerprinting for human miR302/367 induced iPS clones-Cell Line Genetics analysis

|  | BJ | | K2 | | K5 | | K7 | |
|---|---|---|---|---|---|---|---|---|
| amelogenin | X | Y | X | Y | X | Y | X | Y |
| vWA | 16 | 18 | 16 | 18 | 16 | 18 | 16 | 18 |
| D8S1179 | 9 | 11 | 9 | 11 | 9 | 11 | 9 | 11 |
| TPOX | 10 | 11 | 10 | 11 | 10 | 11 | 10 | 11 |
| FGA | 22 | 23 | 22 | 23 | 22 | 23 | 22 | 23 |
| D3S1358 | 14 | 16 | 14 | 16 | 14 | 16 | 14 | 16 |
| THO1 | 7 | 8 | 7 | 8 | 7 | 8 | 7 | 8 |
| D2S11 | 29 | | 29 | | 29 | | 29 | |
| D18S51 | 17 | 19 | 17 | 19 | 17 | 19 | 17 | 19 |
| Penta E | 7 | 17 | 7 | 17 | 7 | 17 | 7 | 17 |
| D5S818 | 12 | | 12 | | 12 | | 12 | |
| D13S317 | 8 | 9 | 8 | 9 | 8 | 9 | 8 | 9 |
| D7S820 | 11 | 12 | 11 | 12 | 11 | 12 | 11 | 12 |
| D16S539 | 9 | 13 | 9 | 13 | 9 | 13 | 9 | 13 |
| CSF1PO | 10 | 12 | 10 | 12 | 10 | 12 | 10 | 12 |
| Penta D | 12 | 13 | 12 | 13 | 12 | 13 | 12 | 13 |

```
SEQUENCE LISTING

<160> NUMBER OF SEQ ID NOS: 10

<210> SEQ ID NO 1
<211> LENGTH: 23
<212> TYPE: RNA
<213> ORGANISM: Homo sapiens

<400> SEQUENCE: 1
uaagugcuuc cauguuuuag uag                                              23

<210> SEQ ID NO 2
<211> LENGTH: 23
<212> TYPE: RNA
<213> ORGANISM: Homo sapiens

<400> SEQUENCE: 2
acuuuaacau ggaagugcuu ucu                                              23

<210> SEQ ID NO 3
<211> LENGTH: 23
<212> TYPE: RNA
<213> ORGANISM: Homo sapiens

<400> SEQUENCE: 3
uaagugcuuc cauguuucag ugg                                              23

<210> SEQ ID NO 4
<211> LENGTH: 22
<212> TYPE: RNA
<213> ORGANISM: Homo sapiens

<400> SEQUENCE: 4
uuuaacaugg ggguaccugc ug                                               22

<210> SEQ ID NO 5
<211> LENGTH: 23
<212> TYPE: RNA
<213> ORGANISM: Homo sapiens

<400> SEQUENCE: 5
uaagugguuc cauguuuugg uga                                              23

<210> SEQ ID NO 6
<211> LENGTH: 22
<212> TYPE: RNA
<213> ORGANISM: Homo sapiens

<400> SEQUENCE: 6
uaaacgugga uguacuugcu uu                                               22

<210> SEQ ID NO 7
<211> LENGTH: 23
<212> TYPE: RNA
<213> ORGANISM: Homo sapiens

<400> SEQUENCE: 7
```

```
uaagugcuuc cauguuugag ugu                                          23

<210> SEQ ID NO 8
<211> LENGTH: 22
<212> TYPE: RNA
<213> ORGANISM: Homo sapiens

<400> SEQUENCE: 8
aauugcacuu uagcaauggu ga                                           22

<210> SEQ ID NO 9
<211> LENGTH: 22
<212> TYPE: RNA
<213> ORGANISM: Homo sapiens

<400> SEQUENCE: 9
acuguugcua auaugcaacu cu                                           22

<210> SEQ ID NO 10
<211> LENGTH: 23
<212> TYPE: RNA
<213> ORGANISM: Homo sapiens

<400> SEQUENCE: 10
gaauugcacu uuagcaaugg uga                                          23
```

MICRORNA INDUCTION OF PLURIPOTENTIAL STEM CELLS AND USES THEREOF

CROSS-REFERENCE TO RELATED APPLICATIONS

This application is a National Phase Application of PCT International Application No. PCT/US11/30012, International Filing Date Mar. 25, 2011, claiming claims priority to U.S. Provisional Patent Application 61/325,596, filed Apr. 19, 2010, each of which is incorporated by reference herein in its entirety.

GOVERNMENT INTEREST

This invention was made in whole or in part with government support under Grant Numbers HL087825 and HL100405, awarded by the National Institutes of Health. The government may have certain rights in the invention

FIELD OF THE INVENTION

The invention provides compostions and methods for inducing the formation of an induced pluripotential stem (iPS) cell from a somatic cell in order to treat a disease or condition in a subject. Specifically, the invention provides inducing the formation of iPS cell from a somatic cell by contacting the somatic cell with a microRNA (miR) 302-367 is cluster or a miR 302-367 cluster mimic.

BACKGROUND OF THE INVENTION

Embryonic stem (ES) cells are stem cells established from early embryos which may be cultured over a long period of time while maintaining pluripotentiality; i.e. the ability to differentiate into any cell type of the body. Using these properties, human embryonic stem cells may be used for cell transplantation therapies for various diseases such as Parkinson's disease, juvenile diabetes, leukemia, and other debilitating human diseases. However, transplantation of ES cells may result in rejection in the same manner as organ transplantation. Moreover, from an ethical viewpoint, there are many who contest the use of ES cells, which are established by destroying human embryos.

If dedifferentiation of patients' own differentiated somatic cells could be induced to establish cells having pluripotency and growth ability similar to those of ES cells (hereinafter, "induced pluripotent stem cells" or "iPS cells,"), they would not only offer the prospect of producing patient-specific cells but also circumvent the ethical conundrum that surrounds the isolation of human embryonic stem (ES) cells from early embryos.

Induced pluripotent stem (iPS) cells have been generated using Oct3/4, Sox2, Klf4, and c-Myc (SOKM; Takahashi et al., Cell 126:663-76, 2006). However, published methods for nuclear reprogramming mediated by the introduction of genes are challenged by low efficiency, in which only a small number of induced pluripotent stem cells can be obtained, and by a slow time course (>7 days). In addition, some of the factors are oncogenic (c-Myc and others). Therefore, a method of generating iPS cells from somatic cells for gene therapy and other uses at high efficiency while avoiding the use of tumorogenic factors is lacking in the art.

MicroRNAs (miRNAs) are small endogenous RNA molecules (~21-25 nt) that to regulate gene expression by targeting one or more mRNAs for translational repression or cleavage. They are small inhibitory RNAs capable of suppressing the translation of target genes with high complementarity. Several thousand miRNAs have been identified in organisms as diverse as viruses, worms, and primates through cloning or computational prediction.

The miR-302-367 cluster has high intracellular abundance and is cell type specific to embryonic stem cells. This miRNA-302-367 cluster was initially identified from cDNA libraries generated by directional cloning using size-fractionated RNA (17-26 nt) from undifferentiated hESCs. This cluster is codified in the human chromosome 4 and comprises nine different miRNAs co-transcribed in a polycistronic manner: miR-302a, miR-302a*, miR-302b, miR-302b*, miR-302c, miR-302c*, miR-302d, miR-367 and miR-367*. The miR-302 family contains seven miRNAs with a highly conserved 5' region. The miR-302-367 cluster was first identified to be expressed in mESC, hESC and in their malignant counterparts hECCs.

The miR-302-367 genes can target over 445 human genes, most of which are developmental signals involving the initiation and/or facilitation of lineage-specific cell differentiation during early human embryogenesis. These target genes are listed in the target prediction sites linked to the miRBase:: Sequences program at the Sanger website, including TARGETSCAN and PICTAR-VERT.

It is unknown if the miR-302-367 cluster can reprogram normal somatic cells at high efficiency. There exists a need for improved miRNA-based compositions and methods for inducing pluripotent cells.

SUMMARY OF THE INVENTION

In another embodiment, the present invention provides a method of inducing the formation of an induced pluripotential stem (iPS) cell from a somatic cell, the method comprising contacting said somatic cell with a composition comprising a) an isolated nucleic acid comprising a microRNA (miR) 302-367 cluster or a miR 302-367 cluster mimic and optionally b) valproic acid.

In another embodiment, the present invention provides a method of inducing the formation of a differentiated cell of interest from a somatic cell, the method comprising contacting said somatic cell with a composition comprising a) an isolated nucleic acid comprising a microRNA (miR) 302-367 cluster and optionally b) valproic acid, thereby inducing the formation of an induced pluripotential stem (iPS) cell and then contacting said iPS cell with a composition for inducing differentiation of said iPS cell into said differentiated cell of interest In another embodiment, the present invention provides a method of increasing the is efficiency of nuclear reprogramming of a somatic cell, comprising contacting said somatic cell with a composition comprising a) an isolated nucleic acid comprising a microRNA (miR) 302-367 cluster and optionally b) valproic acid.

In another embodiment, the present invention provides a method of treating a disease or condition in a subject comprising 1) contacting a somatic cell with a composition comprising a) an isolated nucleic acid comprising a microRNA (miR) 302-367 cluster and optionally b) valproic acid, to yield an induced pluripotential stem (iPS) cell; 2) growing additional iPS cells; 3) inducing differentiation of said iPS cells, 4) contacting said subject with said differentiated cells, thereby treating said disease or condition in said subject.

In another embodiment, the present invention provides a method of treating a disease or condition in a subject comprising 1) contacting said subject with a composition comprising a) an isolated nucleic acid comprising a microRNA (miR) 302-367 cluster and optionally b) valproic acid, to induce the local formation of induced pluripotential stem (iPS) cells, and 2) inducing differentiation of said iPS cells into a healthy cell lineage, thereby treating said disease in said subject.

In another embodiment, the present invention provides an iPS cell produced by a method comprising contacting a somatic cell with a composition comprising a) an isolated nucleic acid comprising a microRNA (miR) 302-367 cluster or a miR 302-367 cluster mimic and optionally b) valproic acid, under conditions sufficient to produce an iPS cell from the somatic cell.

In one embodiment, the present invention provides a composition comprising a) an isolated nucleic acid comprising a microRNA (miR) 302-367 cluster or a miR 302-367 cluster mimic and optionally b) valproic acid.

Other features and advantages of the present invention will become apparent from the following detailed description examples and figures. It should be understood, however, that the detailed description and the specific examples while indicating preferred embodiments of the invention are given by way of illustration only, since various changes and modifications to within the spirit and scope of the invention will become apparent to those skilled in the art from this detailed description.

BRIEF DESCRIPTION OF THE DRAWINGS

The invention will be better understood from a reading of the following detailed description taken in conjunction with the drawings.

FIG. 15. The miR302/367 virus is integrated into the genome and miR302/367 iPS cell clones do not contain Oct4, Sox2, Klf4, or Myc expressing viruses. PCR was used on genomic DNA from miR302/367 mouse clones C6, C7, and C10 (A) and K1, K2, and K5 human clones (B) to show presence of the miR302/367 lentivirus and absence of any other reprogramming viruses. Primers used are listed in Table 1.

FIG. 18. DNA fingerprinting of human miR302/367 iPS cell clones generated from the human foreskin cell line BJ. Fingerprinting was performed by Cell Line Genetics LLC.

DETAILED DESCRIPTION OF THE INVENTION

Figure 1:
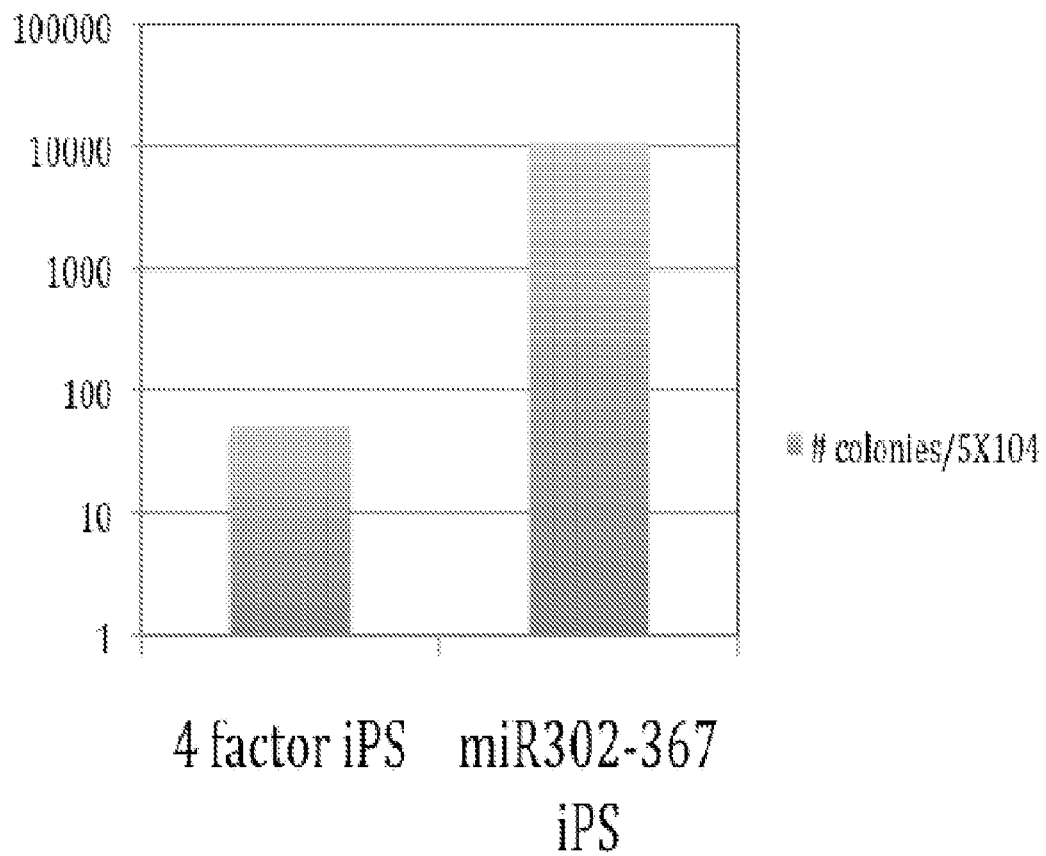
FIG. 1. By day 4 post viral transduction, the efficiency of colony formation with miR302-367 induced pluripotent stem (iPS) cells is more than 20% (50,000 mouse embryonic fibroblasts (MEFs) transduced for 4 factor and miR302-367 lentiviruses). This is compared to an average of 0.1% as reported previously. Moreover, we observe colonies at day 4 and the 0.1% 4 factor average is after 7-14 days. Note that the data are graphed on a logarithmic scale.

In one embodiment, the present invention provides a composition comprising an isolated nucleic acid comprising a microRNA (miR) 302-367 cluster. In another embodiment, the present invention provides a composition consisting of an isolated nucleic acid comprising a microRNA (miR) 302-367 cluster. In another embodiment, the present invention provides a composition comprising an isolated nucleic acid consisting essentially of a microRNA (miR) 302-367 cluster.

In another embodiment, the present invention provides a composition comprising a) an isolated nucleic acid comprising a microRNA (miR) 302-367 cluster and optionally b) a histone deacetylase (HDAC) inhibitor. In another embodiment, the present invention provides a composition comprising a) an isolated nucleic acid comprising a microRNA (miR) 302-367 cluster and optionally b) valproic acid.

In one embodiment, a miR cluster is a genetic region or locus that contains a plurality of microRNAs. In one embodiment, a miR cluster is a group of adjacent genes, which in one embodiment, are co-transcribed in a polycistronic manner. In one embodiment, the miR genes in a cluster are transcribed under the control of a single promoter. In another embodiment, a miR cluster is a group of adjacent and related genes. In one embodiment, a miR 302-367 cluster is a single sequence having multiple miRs, all corresponding to the 302-367 locus.

In one embodiment, a microRNA (miR) 302-367 cluster comprises nine different miRNAs co-transcribed in a polycistronic manner: miR-302a, miR-302a*, miR-302b, miR-302b*, miR-302c, miR-302c*, miR-302d, miR-367 and miR-367*. In one embodiment, the nucleic acid sequence of miR-302b is: UAAGUGCUUCCAUGUUUUAGUAG (SEQ ID NO: 1) (miRBase Accession No: MI0000772; ENTREZ-GENE: 442894). In one embodiment, the nucleic acid sequence of miR-302b* is: ACUUUAACAUG-GAAGUGCUUUCU (SEQ ID NO: 2) (miRBase Accession No: MIMAT0000714). In one embodiment, the nucleic acid sequence of miR-302c is: UAAGUGCUUCCAUGUUU-CAGUGG (SEQ ID NO: 3) (miRBase Accession No: MI0000773; ENTREZGENE: 442895). In one embodiment, the nucleic acid sequence of miR-302c* is: UUUAA-CAUGGGGGUACCUGCUG (SEQ ID NO: 4) (miRBase Accession No: MIMAT0000716). In one embodiment, the nucleic acid sequence of miR-302a is: UAAGUGGUUC-CAUGUUUUGGUGA (SEQ ID NO: 5) (miRBase Accession No: MI0000738; ENTREZGENE: 407028). In one embodiment, the nucleic acid sequence of miR-302a* is: UAAACGUGGAUGUACUUGCUUU (SEQ ID NO: 6) (miRBase Accession No: MIMAT0000683). In one embodiment, the nucleic acid sequence of miR-302d is: UAAGUGCUUCCAUGUUUGAGUGU (SEQ ID NO: 7) (miRBase Accession No: MI0000774; ENTREZGENE: 442896). In one embodiment, the nucleic acid sequence of miR-367 is as follows AAUUGCACUUUAGCAAUG-GUGA (SEQ ID NO: 8) (miRBase Accession No: MIMAT0004686; ENTREZGENE: 442912). In one embodiment, the nucleic acid sequence of miR-367* is as follows ACUGUUGCUAAUAUGCAACUCU (SEQ ID NO: 9) (miRBase Accession No: MI0000772).

In another embodiment, the nucleic acid sequence is a homolog of the sequence described hereinabove. In one embodiment, the homolog is as described in PCT Patent Publication No: WO/2009/091659, which is incorporated by reference herein in its entirety, or another homolog known in the art. In another embodiment, the nucleic acid sequence is a homolog that improves the binding strength, specificity, function or a combination thereof, of the miRNA. In another embodiment, the nucleic acid sequence is a fragment of the sequence described hereinabove, which in one embodiment, is a functional fragment.

Nucleic acids described herein may be replaced by their functionally equivalent fragments or homologs, which in one embodiment, have at least 50%, 60%, 70%, 80%, 90%, 95%, or 98% sequence homology. In particular, mir-302a, mir-302b, mir-302c, and mir-302d genes and RNAs described herein may be replaced with other genes and RNAs with similar functions such as mir-302a* mir-302b*, mir-302c*, mir-367, mir-93, mir-371, mir-372, mir-373, mir-520, and the like.

In one embodiment, the miR302-367 cluster for use in the compositions and methods of the present invention is the entire miR302-367 locus. In another embodiment, the miR302-367 cluster for use in the compositions and methods of the present invention is the miR302-367 gene cluster intron. In another embodiment, the miR302-367 cluster for use in the compositions and methods of the present invention is the first 1234 nucleotides of the miR302-367 gene cluster. In another embodiment, the miR302-367 cluster for use in the compositions and methods of the present invention is a recombinant gene comprising miR302b, miR302c, miR302a, miR302d and miR367 linked so as to be transcribed as a single unit. In one embodiment, only the genes encoding the miRs are included in the miR 302-367 cluster, while in another embodiment, intronic sequences between and adjacent to the genes encoding the miRs are included in the miR 302-367 cluster. In another embodiment, the miR302-367 cluster is a 644 bp fragment of the human miR302-367 region or a 690 bp fragment of the mouse miR302-367 region. In another embodiment, the miR302-367 cluster is the intronic region between exons 8 and 9 of the Larp7 gene as denoted on the Ensembl database.

In one embodiment, the mir-302 members share an identical (100%) sequence in their 5' first seventeen (17) nucleotides, including the entire seed motif, and an overall 83%-96% homology in their 23-nucleotide mature miRNA sequences. The seed motif is located in the first 5' eight nucleotides of a mature miRNA sequence, which determines the binding specificity and efficiency between the miRNA and its target genes. Based on the prediction of 'TAR-GETSCAN" (http://www.targetscan.org/) and "PICTAR-VERT" (http://pictar.bio.nyu.edu/cgi-bin/PicTar_vertebrate-.cgi?) programs linked to the Sanger miRBase:: Sequences website (http://microrna.sanger.ac.uk/), they are directed against almost the same cellular genes, including over 445 conserved genes in human and mouse. Most of these target genes are developmental signals and transcriptional factors involved in initiation and/or facilitation of lineage-specific cell differentiation during early embryogenesis (Lin et al, (2008b) RNA 14: 2115-2124). Many of these target genes are also well-known oncogenes. For example, the mir-302/367 cluster targets, inter alia, eighteen members of the IGF receptor (IGFR)-Ras/PI3K signaling pathways where insulin-like growth factors (IGF) are potent developmental signals for the differentiation of neuron-specific cell lineage via either the Ras/Raf/mitogen-activated protein kinase (MAPK) or the is phosphatidylinositol 3-kinase (PI3K)/Akt signal transduction pathway, which is the same signaling pathways involved in many tumor/cancer transformations, such as brain tumor, breast cancer, lung cancer, prostate cancer, and skin melanoma. Thus, in one embodiment, the compositions and methods of the present invention may be used to suppress tumors or tumor formation.

In one embodiment, the methods of the present invention may be used with miRNA families other than miR-302-367 that are specifically expressed in ES cells to induce reprogramming of somatic cells to iPS. According to this aspect and in one embodiment, the miRNA family is miR290/295 cluster on chromosome 7 in mouse. In another embodiment, the miRNA family is hsa-miR-372 (MI0000780), hsa-miR-373 (MI0000781), or hsa-miR-373/373*; hsa-miR-371-373 cluster; hsa-miR-520c (MI0003158), or hsa-miR-520c-5p/520c-3p; mmu-miR-290 (MI0000388), mmu-miR-291a (MI0000389), or mmu-miR-291a-5p/291a-3p; mmu-miR-294 (MI0000392), or mmu-miR-294/294*; and mmu-miR-295 (MI0000393), or mmu-miR-295/295* or others described in Suh et al. 2004 (Dev. Biol. 270:488-498, incorporated herein by reference in its entirety) or otherwise known in the art. In one embodiment, a combination of the above-referenced miRs may be used in the compositions and methods of the present invention. This list is not to be construed as limiting, and other miRNA families highly and specifically expressed in ES cells may be used in the methods of the present invention.

In one embodiment, the following miRNAs may be used in the compositions and methods of the present invention, either instead of or in addition to miR-302-367 to promote iPS generation: miR106, miR20a/b, miR93, miR17-92 cluster, or a combination thereof.

In one embodiment, the present invention provides a composition comprising a) an isolated nucleic acid comprising a microRNA (miR) 302-367 cluster mimic and b) a histone deacetylase (HDAC) inhibitor.

In one embodiment, a microRNA mimic is used in the compositions and methods of the present invention. In one embodiment, the mimic is a double-stranded oligonucleotide designed to mimic the function of endogenous mature miRNA. In one embodiment, an miRNA mimic may comprise one or more chemical modifications that enhances the stability and/or functionality of the duplex. In one embodiment, the modification, which in one embodiment comprises 2'-O-methyl modification of some or all of the nucleotides of the sense strand, minimizes the nuclease sensitivity of the strand and enhance the entry of the antisense strand into the RNA interference silencing complex (RISC). In another is embodiment, the mimic is chemically enhanced to preferentially program RNA-Induced Silencing Complex (RISC) with the active miRNA strand. In one embodiment, an miRNA mimic may comprise one or more chemical modifications as described in United States Patent Application Publication No. 2007/0269889, incorporated herein by reference in its entirety. In one embodiment, a mimic for use in the compositions and methods of the present invention is commercially available, in one embodiment, from Dharmacon or Qiagen. In one embodiment, the mimic is a cholesterol-modified mimic. In one embodiment, the mimic enables non viral mediated miRNA expression. In one embodiment, the mimic is a small and active version of a microRNA. In another embodiment, the mimic is a non-natural double-stranded miRNA-like RNA fragment, which in one embodiment is designed to have it s 5 end bearing a partially complementary motif to the selected sequence in the 3 UTR unique to the target gene. In one embodiment, this RNA fragment can specifically bind its target gene in a gene-specific fashion. In one embodiment, the mimic is a multi-miRNA mimic, which, in one embodiment, is able to silence multiple genes. In one embodiment, the mimic is a multi-miRNA mimic, as described in Wang 2009 (Multi-miRNA Hairpins and Multi-miRNA Mimics Technologies in MicroRNA Interference Technologies, Springer Berlin Heidelberg).

In one embodiment, one or more pre-miRNA precursors are used in the compositions and methods of the present invention. The pre-mRNA precursor may act to gain function for the miRNA. Any form of a pre-mRNA precursor can be used.

In some embodiments, when a mimic or pre-miRNA precursor is used, one or more mimics or pre-miRNA precursors can be used instead of all in the cluster.

In one embodiment, iPS cells produced using compositions and methods of the present invention may be grown in cell culture in feeder-free cell culture conditions, which in one embodiment, decreases the risk of transferring animal or human viruses to iPS cells.

In one embodiment, the compositions and methods of the present invention utilize a histone deacetylase (HDAC) inhibitor. In one embodiment, the HDAC inhibitor is valproic acid. Other HDAC inhibitors are known in the art and are to be considered part of the invention described herein. In one embodiment, the HDAC inhibitor interferes with the function of histone deacetylase to remove the acetyl groups from the lysine residues leading to the formation of a condensed and transcriptionally silenced chromatin.

In one embodiment, a HDAC inhibitor of the present invention is a Hydroxamates, Short chain fatty acid, Benzamide, Cyclic tetrapeptide, Sulfonamide anilide, or other.

In one embodiment, a HDAC inhibitor of the present invention is Trichostatin A is (TSA), Suberoylanilide hydroxamic acid (SAHA, vorinostat), LBH589 (panobinostat), PCI24781 (CRA-024781), LAQ824, PXD101 (belinostat), ITF2357, SB939, JNJ-16241199 (R306465), m-carboxycinnamic acid bishydroxamide (CBHA), Scriptaid, Oxamflatin, Pyroxamide, or Cyclic hydroxamic acid containing peptides (CHAPs). In another embodiment, a HDAC inhibitor of the present invention is Butyrate, Valproate, AN-9, or OSU-HDAC42. In another embodiment, a HDAC inhibitor of the present invention is MS-275 (entinostat), MGCD0103, Pimelic diphenylamide, M344, or N-acetyldinaline (CI-994). In another embodiment, a HDAC inhibitor of the present invention is Apicidine, Trapoxins (in one embodiment, trapoxin B), HC-toxin, Chlamydocin, or Depsipeptide (FR901228 or FK228) (romidepsin). In another embodiment, a HDAC inhibitor of the present invention is N-2-aminophenyl-3-[4-(4-methyl-benzenesulfonylamino)-phenyl]-2-propenamide. In another embodiment, a HDAC inhibitor of the present invention is Depudecin, NDH-51, or KD5150.

In one embodiment, a HDAC inhibitor of the present invention is a "classical" HDAC inhibitor, which in one embodiment, acts on Class I and Class II HDACs by binding to the zinc containing catalytic domain of the HDACs. In one embodiment, a HDAC inhibitor of the present invention is a one embodiment), a depsipeptide, an electrophilic ketone, or an aliphatic acid compound (in one embodiment, phenylbutyrate or valproic acid).

In another embodiment, a HDAC inhibitor of the present invention is a "second generation" HDAC inhibitor, which in one embodiment, is mocetinostat, (MGCD0103). In another embodiment, a HDAC inhibitor of the present invention is an inhibitor of Class III HDACs, which in one embodiment is nicotinamide, and in another embodiment, NAD, dihydrocoumarin, naphthopyranone, or 2-hydroxynaphaldehyde.

A number of structural classes of negative regulators of HDACs (e.g., HDAC inhibitors) have been developed, for example, small molecular weight carboxylates (e.g., less than about 250 amu), hydroxamic acids, benzamides, epoxyketones, cyclic peptides, and hybrid molecules. (See, for example, Drummond D C, Noble C O, Kirpotin D B, Guo Z, Scott G K, et al. (2005) Clinical development of histone deacetylase inhibitors as anticancer agents. Annu Rev Pharmacol Toxicol 45: 495-528, (including specific examples therein) which is hereby incorporated by reference in its entirety). Non-limiting examples of negative regulators of type I/II HDACs include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (i.e., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-C1-UC HA (i.e., 6-(3-chlorophenylureido)caproic hydroxamic acid), AOE (2-amino-8-oxo-9,10-epoxydecanoic acid), CHAP31 and CHAP 50. Other inhibitors include, for example, dominant negative forms of the HDACs (e.g., catalytically inactive forms) siRNA inhibitors of the HDACs, and antibodies that specifically bind to the HDACs. Inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

In some embodiments, HDAC inhibitor (e.g., valproic acid) is not necessary for inducing the formation of an induced pluripotential stem (iPS) cell. For example, in human cells, valproic acid is not needed for reprogramming.

In one embodiment, the present invention provides a composition comprising a) an isolated nucleic acid comprising a microRNA (miR) 302-367 cluster or a miR 302-367 cluster mimic and optionally b) a histone deacetylase (HDAC) inhibitor. In another embodiment, the present invention provides an isolated nucleic acid comprising a microRNA (miR)

302-367 cluster. In another embodiment, the present invention provides an isolated nucleic acid comprising a microRNA (miR) 302-367 cluster mimic.

In one embodiment, the concentration of HDAC inhibitor is 2 mM. In another embodiment, the concentration of HDAC inhibitor is 1-3 mM. In another embodiment, the concentration of HDAC inhibitor is 1-5 mM. In another embodiment, the concentration of HDAC inhibitor is 0.5-2 mM.

In one embodiment, the term "isolated nucleic acid" includes nucleic acid molecules to that are separated from other nucleic acid molecules that are present in the natural source of the nucleic acid. For example, with respect to genomic DNA, the term "isolated" includes nucleic acid molecules that are separated from the chromosome with which the genomic DNA is naturally associated. In one embodiment, an "isolated" nucleic acid is free of sequences that naturally flank the nucleic acid (i.e., sequences located at the 5' and/or 3' ends is of the nucleic acid) in the genomic DNA of the organism from which the nucleic acid is derived. Moreover, in one embodiment, an "isolated" nucleic acid molecule, such as a cDNA molecule, is substantially free of other cellular material, or culture medium when produced by recombinant techniques, or substantially free of chemical precursors or other chemicals when chemically synthesized.

In one embodiment, a nucleic acid of the present invention comprises a recombinant sequence. In one embodiment, a "recombinant" sequence refers to a sequence that does not occur in nature.

In one embodiment, to monitor the transcription of the recombinant sequence and subsequent processing of the transcript, a detectable marker gene may be used, wherein a recombinant sequence comprises at least two exons, together encoding a marker gene flanking one intron encoding one or more mir302-367 genes. In one embodiment, a marker or reporter gene encoded by the combination of the two exons described hereinabove is fluorescent protein (GFP) genes, luciferase genes, lac-Z genes, viral genes, bacterial genes, plant genes, animal genes, human genes, or a combination thereof. In one embodiment, the intron comprising the mir302-367 genes is spliced out, allowing expression of the reporter gene(s).

In another embodiment, the present invention provides an expression vector comprising an isolated nucleic acid comprising a microRNA (miR) 302-367 cluster. In another embodiment, the present invention provides an expression vector comprising an isolated nucleic acid comprising a microRNA (miR) 302-367 cluster mimic.

In one embodiment, a nucleic acid of the invention can be included in a vector, preferably an expression vector. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication to defective retroviruses, adenoviruses, lentiviruses, and adeno-associated viruses. Thus, in one embodiment, the nucleic acid sequence encoding the miR-302-367 cluster or miR-302-367 cluster mimic is present within a vector. In one embodiment, the vector is a viral vector, which in one embodiment is a lentivirus vector, and, in another embodiment, the vector is a plasmid vector.

A vector can include a nucleic acid of the invention in a form suitable for the expression of the nucleic acid in a host cell. The design of the expression vector can depend on such factors as the choice of the host cell to be transformed, the level of miR-302-367 gene expression desired, and the like. The expression vectors of the invention can be introduced into host cells to thereby produce miR-302-367.

In one embodiment, a nucleic acid or vector of the invention can be introduced into host cells via conventional transformation or transfection techniques. As used herein, the terms "transformation" and "transfection" are intended to refer to a variety of art-recognized techniques for introducing a foreign nucleic acid (e.g., DNA) into a host cell, including, inter alia, calcium phosphate or calcium chloride co-precipitation, DEAE-dextran-mediated transfection, lipofection, or electroporation.

The expression vectors of the invention can be designed for the expression of the miR-302-367 genes in a variety of cells such as insect cells (e.g., using baculovirus expression vectors), yeast cells, or mammalian cells. Suitable host cells are discussed further in Goeddel, Gene Expression Technology: Methods in Enzymology 185, Academic Press, San Diego, Calif. (1990). Alternatively, the expression vector can be transcribed in vitro, for example using T7 promoter regulatory sequences and T7 polymerase.

In one embodiment, the expression vector's control functions are provided by viral regulatory elements when used in mammalian cells. For example, commonly used promoters are derived from polyoma, Adenovirus 2, cytomegalovirus and Simian Virus 40. In some embodiments, an expression vector of the invention is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application is Publication No. 264,166). Developmentally-regulated promoters are also encompassed, including for example, the murine hox promoters (Kessel and Gruss (1990) Science 249:374-379) and the α-fetoprotein promoter (Campes and Tilghman (1989) Genes Dev. 3:537-546).

In one embodiment, viral vectors used in the methods of the present invention comprise Cre-lox sites so that expression of Cre-recombinase will remove viral vectors or a portion thereof from the host cell genome. Such Cre-lox systems are known in the art. In another embodiment, piggyBac transposon/transposase system is used to insert transgenes into the host cell genome. After pluripotency has been established, expression of piggyBac transposase removes the transgenes and the piggyback terminal repeats, leaving no residual trace of genomic integration. In another embodiment, adenoviral vectors may be used to deliver the nucleic acids of the present invention, wherein adenoviruses do not integrate into the host genome. In another embodiment, expression plasmids are used to transiently transfect cells and generate iPS cells. In another embodiment, an expression plasmid such as the one described in PCT Patent Publication No: WO/2009/091659, which is incorporated herein by reference in its entirety, is used.

In one embodiment, the miR302-367 cluster of the present invention is operably linked to a regulatory sequence. In one embodiment, the term "regulatory sequence" or "regulatory element" includes promoters, enhancers and other expression control elements (e.g., polyadenylation signals). Regulatory sequences include those that direct constitutive expression of a nucleotide sequence, as well as tissue-specific regulatory and/or inducible sequences. Thus, in one embodiment, the miR302-367 cluster of the present invention is operably linked to a constitutive promoter, while in another embodiment, the miR302-367 cluster of the present invention is operably linked to an inducible promoter. In one embodiment, the inducible promoter is a doxycycline inducible promoter.

The invention further provides a host cell that includes a nucleic acid of the invention. The nucleic acid may be within an expression vector or homologously recombined into a specific site of the host cell's genome. The terms "host cell" refers not only to the particular subject cell but to the progeny or potential progeny of such a cell.

In another embodiment, the present invention provides a host cell comprising an isolated nucleic acid comprising a microRNA (miR) 302-367 cluster. In another embodiment, the present invention provides a host cell comprising an isolated nucleic acid comprising a microRNA (miR) 302-367 cluster mimic.

A host cell of the invention can be used to produce miR-302-367. Accordingly, the is invention further provides methods for producing miR-302-367 using the host cells of the invention. In one embodiment, the method includes culturing the host cells of the invention in a suitable medium such that miR-302-367 is produced.

In another embodiment, the present invention provides a transgenic animal comprising an isolated nucleic acid comprising a microRNA (miR) 302-367 cluster. In another embodiment, the present invention provides a transgenic animal comprising an isolated nucleic acid comprising a microRNA (miR) 302-367 cluster mimic. In one embodiment, the nucleic acid comprises a cre-lox recombination site.

The invention additionally features non-human transgenic animals containing a nucleic acid of the invention. Such animals are useful for studying the function and/or activity of miR-302-367. As used herein, a "transgenic animal" is a non-human animal, preferably a mammal, more preferably a rodent such as a rat or mouse, in which one or more of the cells of the animal include a transgene containing a nucleic acid of the invention. Other examples of transgenic animals include non-human primates, sheep, dogs, cows, goats, chickens, amphibians, and the like. A transgene is an exogenous nucleic acid, which preferably is integrated into the genome of the cells of a transgenic animal. A transgene can direct the expression of an encoded gene product in one or more cell types or tissues of the transgenic animal.

Intronic sequences and polyadenylation signals may also be included in the transgene to increase the efficiency of the expression of the transgene. A tissue-specific regulatory sequence may be operably linked to a transgene of the invention to direct the expression of miR-302-367 to particular cells. A transgenic founder animal can be identified, based upon the presence of a transgene in its genome and/or expression of miR-302-367 in tissues or cells of the animal. A transgenic founder animal can then be used to breed additional animals carrying the transgene. Moreover, transgenic animals carrying a transgene can further be bred to other transgenic animals carrying other transgenes. The invention also provides a population of cells from a transgenic animal, as discussed herein.

In one embodiment, a methyltransferase inhibitor, which in one embodiment, is 5-aza-cytidine (AZA) may be used in the methods of the present invention. In one embodiment, AZA drives partially reprogrammed cells to fully reprogrammed iPS cells. In another embodiment, a DNA methyl transferase inhibitor may be use in place of or in addition to the HDAC inhibitor in any of the compositions and methods of the present invention.

In one embodiment, the compositions and methods of the present invention increase efficiency of iPS generation by two orders of magnitude. In another embodiment, the efficiency is increased by one order of magnitude. In another embodiment, the efficiency is increased by 100%. In another embodiment, the efficiency is increased by 50%. In another embodiment, the efficiency is increased by 75%. In another embodiment, the efficiency is 2 times higher. In another embodiment, the efficiency is 5 times higher. In another embodiment, the efficiency is 10 times higher. In another embodiment, the efficiency is 20 times higher. In another embodiment, the efficiency is 50 times higher. In another embodiment, the efficiency is 100 times higher. In another embodiment, the efficiency is 200 times higher. In another embodiment, the efficiency is 500 times higher. In another embodiment, the efficiency is 2 times higher. In another embodiment, the efficiency is 1000 times higher.

In one embodiment, the number of stem cells produced, in the presence of mir-302-367 and a histone deactylase (HDAC) inhibitor is 5-, 10-, 15-, 20-, 25-, 30-, 35-, 40-, 50-, 100-, 120-, 130-, 140-, 150-, 200-, 250-, 500-, 750- or 1000-fold greater than the number of stem cells produced by alternative methods, e.g., the number of stem cells produced by cell expressing one or more transcription factors, e.g., Oct4 and Sox2, or Oct4, Klf4 and Sox2 or Oct4, Klf4, Sox2 and c-Myc.

In another embodiment, the efficiency is 20% (FIG. 1). In another embodiment, the efficiency is 10-30%. In another embodiment, the efficiency is 5-50%. In another embodiment, the efficiency is greater than 15%. In another embodiment, the efficiency is 15-25%. In another embodiment, the efficiency is 17-22%. In another embodiment, the efficiency is greater than 1%. In another embodiment, the efficiency is greater than 2%. In another embodiment, the efficiency is greater than 5%. In another embodiment, the efficiency is greater than 10%. In another embodiment, the efficiency is greater than 2-5%.

In another embodiment, the present invention provides a method of inducing the formation of an induced pluripotential stem (iPS) cell from a somatic cell, the method comprising contacting said somatic cell with a composition comprising a) an isolated nucleic acid comprising a microRNA (miR) 302-367 cluster or a miR 302-367 cluster mimic and b) a histone deacetylase (HDAC) inhibitor.

In one embodiment, a somatic cell for use in the methods and compositions of the present invention are non-cancerous. In one embodiment, non-cancerous somatic cells are is used in the methods of the present invention. In one embodiment, "non-cancerous" refers to a cell that is healthy. In one embodiment, "non-cancerous" refers to a cell that is normal. In another embodiment, "non-cancerous" refers to a cell whose morphology is normal. In another embodiment, "non-cancerous" refers to a cell that does not have markers of being a cancer cell. In another embodiment, "non-cancerous" refers to a cell that is derived from a healthy or normal subject that has not been diagnosed with cancer.

In another embodiment, the present invention provides a method of inducing the formation of a differentiated cell of interest from a non-cancerous somatic cell, the method comprising contacting said somatic cell with a composition comprising a) an isolated nucleic acid comprising a microRNA (miR) 302-367 cluster and b) a histone deacetylase (HDAC)

inhibitor, thereby inducing the formation of an induced pluripotential stem (iPS) cell and then contacting said iPS cell with a composition for inducing differentiation of said iPS cell into said differentiated cell of interest In another embodiment, the present invention provides a method of increasing the efficiency of nuclear reprogramming of a non-cancerous somatic cell, comprising contacting said somatic cell with a composition comprising a) an isolated nucleic acid comprising a microRNA (miR) 302-367 cluster and b) a histone deacetylase (HDAC) inhibitor.

In another embodiment, the present invention provides a method of treating a disease or condition in a subject comprising 1) contacting a somatic cell with a composition comprising a) an isolated nucleic acid comprising a microRNA (miR) 302-367 cluster and b) a histone deacetylase (HDAC) inhibitor to yield an induced pluripotential stem (iPS) cell; 2) growing additional iPS cells; 3) inducing differentiation of said iPS cells, 4) contacting said subject with said differentiated cells, thereby treating said disease or condition in said subject.

In another embodiment, the present invention provides a method of treating a disease or condition in a subject comprising 1) contacting said subject with a composition to comprising a) an isolated nucleic acid comprising a microRNA (miR) 302-367 cluster and b) a histone deacetylase (HDAC) inhibitor to induce the local formation of induced pluripotential stem (iPS) cells, and 2) inducing differentiation of said iPS cells into a healthy cell lineage, thereby treating said disease in said subject.

In one embodiment, the present invention provides a method of inducing the is formation of an induced pluripotential stem (iPS) cell from a somatic cell. In one embodiment, the present invention provides a method of inducing the formation of an induced pluripotential stem (iPS) cell from a non-cancerous somatic cell. In another embodiment, the present invention provides a method of producing an induced pluripotential stem (iPS) cell from a non-cancerous somatic cell. In another embodiment, the present invention provides a method of generating an induced pluripotential stem (iPS) cell from a non-cancerous somatic cell.

In one embodiment, the steps of the methods of the present invention are repeated in order to increase iPS cell production. In one embodiment, the steps of the methods of the present invention are repeated in order to increase the efficiency of iPS cell production. In one embodiment, the steps of the methods of the present invention are repeated in order to increase the speed of iPS cell production.

In one embodiment, the methods of the present invention induce reprogramming of a somatic cell into an iPS cell. In one embodiment, iPS cells exhibit one or more of the following properties: loss of somatic cell-specific markers, expression of the appropriate stage-specific embryonic antigens, telomerase activity, X chromosome reactivation (in female cells), reactivation of endogenous genes essential for pluripotency and self-renewal (e.g. Sox2, Oct4, and Nanog), and silencing of exogenous factors used to initiate reprogramming. Other properties known in the art are to be considered part of the invention.

In some embodiments, the expression of a marker selected from a group consisting of alkaline phophatase, NANOG, OCT4, SOX2, SSEA4, TRA-1-60 and TRA-1-81, is upregulated by a statistically significant amount in the iPS cell relative to the somatic cell.

In one embodiment, alkaline phosphatase may be measured using methods based on enzymatic reaction followed by colorimetric or fast red violet dye, fluorescent detection and immunostaining.

In one embodiment, reprogramming factors are Sox2, Oct4, Klf4, c-Myc, while in to another embodiment, reprogramming factors are Sox2, Oct4, Nanog, and Lin28, while in another embodiment, reprogramming factors are Sox2, Oct4, and Klf4.

In one embodiment, somatic cells are characterized by limited proliferation, pluripotency genes methylated, tissue-specific cell morphology, X-chromosome inactivated, active G1 cell cycle checkpoint, and expression of somatic cell specific markers.

In one embodiment, induced pluripotent stem cells are characterized by self-renewal, pluripotency, embryonic stem cell morphology, demethylation of pluripotency genes, reactivation of pluripotency genes, X-chromosome reactivation, telomerase activity, loss of G1 checkpoint.

In one embodiment, mouse ES/iPS cells require leukemia inhibitory factor (LIF) in culture medium and express stage-specific embryonic antigen (SSEA)-1. In one embodiment, human ES/iPS cells require fibroblast growth factor (FGF) in culture, which in one embodiment, is FGF2 and express SSEA-3 and SSEA-4. Other cell culture requirements and markers for iPS cells are known in the art and are to be considered part of the present invention.

In one embodiment, the compositions and methods of the present invention induce early markers of pluripotency, which in one embodiment, are SSEA-1 and alkaline phosphatase (AP) expression. In one embodiment, the compositions and methods of the present invention induce late markers of pluripotency, which in one embodiment, are reactivation of the inactive X chromosome, reactivation of telomerase activity, reactivation of endogenous Oct4, Nanog, and Sox2 genes, or a combination thereof.

In one embodiment, the compositions and methods of the present invention induce markers of pluripotency, and, in one embodiment, markers of advanced stage of pluripotency, after only 4 days (FIG. 1). In another embodiment, pluripotency markers appear after only 6 days. In another embodiment, pluripotency markers appear less than seven days from transduction of miR302-367. In another embodiment, pluripotency markers appear between 4 and 6 days after transduction of miR302-367. In another embodiment, pluripotency markers appear between 2 and 6 days after transduction of miR302-367.

In one embodiment, hypoxic cell conditions may be used in the methods of the present invention, to, in one embodiment, maintain the pluripotency of iPS cells, upregulate to Oct4, Sox2, and Nanog, and down-regulate the p53 pathway, or a combination thereof. In another embodiment, the Rho-kinase (ROCK) inhibitor Y-27632, may be included in the cell media.

In one embodiment, inhibitors of the p53-p21 pathway may be used in conjunction with the compositions and methods described herein. In another embodiment, inhibition of is miRNA-145 may be used in conjunction with the compositions and methods described herein.

In one embodiment, the present invention provides methods of inducing the formation of an induced pluripotential stem (iPS) cell from a non-cancerous somatic cell, the method comprising contacting said somatic cell with a composition comprising a) an isolated nucleic acid comprising a microRNA (miR) 302-367 cluster or a miR 302-367 cluster mimic and b) a histone deacetylase (HDAC) inhibitor. In one embodiment, a somatic cell for use in any of the compositions or methods of the present invention is a fibroblast cell, which in one embodiment, is an embryonic fibroblast cell. In another embodiment, a somatic cell for use in any of the compositions or methods of the present invention is an adult fibroblast. In another embodiment, a somatic cell for use in any of the compositions or methods of the present invention is a keratinocyte. In another embodiment, a somatic cell for use in any of the compositions or methods of the present invention is a neural progenitor cell. In another embodiment, a somatic cell for use in any of the compositions or methods of the present invention is a hepatocyte. In another embodiment, a somatic cell for use in any of the compositions or methods of the present invention is a stomach epithelial cell. In another embodiment, a somatic cell for use in any of the compositions or methods of the present invention is a pancreatic β cell. In another embodiment, a somatic cell for use in any of the compositions or methods of the present invention is an intestinal epithelial cell. In some embodiments, the somatic cell is a fibroblast (e.g., a primary fibroblast), a muscle cell (e.g., a myocyte), a cumulus cell, a neural cell, a liver cell, a GI tract cell, a mammary cell, or a pancreatic islet cell. In another embodiment, a somatic cell for use in any of the compositions or methods of the present invention is another cell known in the art.

In one embodiment, a somatic cell for use in any of the compositions or methods of the present invention is a human somatic cell. In another embodiment, a somatic cell for use in any of the compositions or methods of the present invention is a murine somatic cell. In another embodiment, a somatic cell for use in any of the compositions or methods of the present invention is a porcine somatic cell. In another embodiment, a somatic cell for use in to any of the compositions or methods of the present invention is a bovine somatic cell. In another embodiment, a somatic cell for use in any of the compositions or methods of the present invention is a non-human primate somatic cell.

In one embodiment, the iPS cell has a normal karyotype.

In one embodiment, the somatic cell is a primary cell or is a progeny of a primary is or secondary cell.

In one embodiment, the somatic cell is obtained from a sample selected from a group consisting of a hair follicle, a blood sample, a swab sample or an adipose biopsy.

In one embodiment, the somatic cell is a healthy cell or a cell containing at least one genetic lesion.

In one embodiment, a plurality of the iPS cells are produced from a plurality of the somatic cells.

In one embodiment, the present invention provides an iPS cell produced by a method comprising contacting a somatic cell with a miR302-367 cluster or a miR302-367 cluster mimic and an HDAC inhibitor under conditions sufficient to produce an iPS cell from the somatic cell.

In one embodiment, iPS cells generated using the methods of the present invention may be used for disease therapy. In another embodiment, iPS cells generated using the methods of the present invention may be used for disease modeling, in one embodiment, to better understand the underlying pathophysiology. In another embodiment, iPS cells generated using the methods of the present invention may be used for patient-specific toxicology studies.

In one embodiment, compositions and methods of the present invention may be used to produce iPS cells for bone marrow transplants to treat leukemia. In one embodiment, compositions and methods of the present invention may be used to produce iPS cells to treat diseases including cancer, Parkinson's disease, muscle damage, burns, heart disease, diabetes, osteoarthritis, rheumatoid arthritis, hematopoietic conditions (e.g., sickle cell anemia, leukemia, lymphoma, inherited blood disorders, immune deficiencies), immune deficiencies), cardiac disorders (e.g., myocardial infarcts, and myopathies) and disorders such as liver disease, diabetes, thyroid abnormalities, neurodegenerative/neurological disorders (e.g., Parkinson's Disease, Alzheimer's Disease, stroke injuries, spinal chord injuries), Crohn's to Disease, circulatory disorders, respiratory disorders, wound healing and/or repair, bone repair, and enzyme abnormalities.

In one embodiment, the cell is contacted with the HDAC inhibitor at the same time as the miR302-367 cluster. In another embodiment, the cell is contacted with the HDAC inhibitor before it is contacted with the miR302-367 cluster. In another embodiment, the cell is contacted with the HDAC inhibitor after it is contacted with the miR302-367 cluster. In one embodiment, the time period between contacting of the cell with the HDAC inhibitor and the miR302-367 cluster is one minute, five minutes 15 minutes, 30 minutes, 1 hour, 6 hours 8 hours, 12 hours, 24 hours, or 2 days.

In one embodiment, the method further comprises the step of contacting the cell with a glucocorticoid compound, which in one embodiment is dexamethasone.

In one embodiment, the method further comprises implanting the iPS cells in to a subject. In one embodiment, the subject is suffering from a disorder. In one embodiment, the iPS cells are from a donor different than the subject (e.g., a relative of the subject).

In one embodiment, a method of the invention may further comprise inducing the iPS cells to differentiate into tissue cell types. Through in vitro manipulations with different factors and/or hormones, iPS cells can differentiate into the three embryonic germ layers (ectoderm, mesoderm and definitive endoderm). Absent any treatment, xenograft implantation of embryoid bodies derived from the iPS cells into an animal or human can form various tissue structures. For example, as described hereinbelow, after in vitro treatments of various growth factors and/or hormones, the miR302-367 cells differentiate into several tissue cell types ex vivo, including cardiac myocytes and hematopoietic cells (Example 6). Xenograft implantation of the miR302-367 cells-derived embryoid bodies into the uterus or peritoneal cavity of female pseudopregnant immunocompromised SCID-beige mice forms teratoma-like primordial tissue structures (Example 3).

In one embodiment, the methods of the present invention produce a cell that is less differentiated from the somatic cell used therein. In one embodiment, the methods of the present invention produce a cell that produces some, but not all, of the iPS markers or characteristics, as described hereinabove and as are known in the art.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects. A subject to be treated may be identified in the judgment of the subject or a health care professional, which can be is subjective (e.g., opinion) or objective (e.g., reached by detecting a cancer marker in the subject).

In one embodiment, a "treatment" is the administration of a substance to a subject with the purpose to cure, alleviate, relieve, remedy, prevent, suppress, inhibit, or ameliorate a disorder, symptoms of the disorder, a disease state secondary to the disorder, or predisposition toward the disorder.

In one embodiment, "treating" refers to either therapeutic treatment or prophylactic or preventative measures, wherein the object is to prevent or lessen the targeted pathologic condition or disorder as described hereinabove, while in another embodiment, "treating" may refer only to therapeutic treatment. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, prolonging patient survival, or a combination thereof.

In one embodiment, an "effective amount" is an amount of a compound that is capable of producing a medically desirable result in a treated subject. The medically desirable result may be objective (i.e., measurable by some test or marker) or subjective (i.e., subject gives an indication of or feels an effect).

In one embodiment, nucleic acids can be delivered to target cells by, for example, the use of polymeric, biodegradable microparticle or microcapsule devices known in the art. Another way to achieve uptake of nucleic acids is to use liposomes, prepared by standard methods. The nucleic acids can be incorporated alone into these delivery vehicles or co-incorporated with tissue-specific or tumor-specific antibodies. In another embodiment, one is can prepare a molecular conjugate composed of a nucleic acid attached to poly-L-lysine by electrostatic or covalent forces. Poly-L-lysine binds to a ligand that can bind to a receptor on target cells. "Naked DNA" (i.e., without a delivery vehicle) can also be delivered to an intramuscular, intradermal, or subcutaneous site. In one embodiment, the preferred dosage for administration of nucleic acids is from approximately $10^6$ to $10^{12}$ copies of the nucleic acid molecule.

In one embodiment, the compositions or methods of the present invention comprise the specified elements or steps. In another embodiment, the compositions or methods of the present invention consist essentially of the specified elements or steps. In another embodiment, the compositions or methods of the present invention consist of the specified elements or steps.

In some embodiments, the term "comprise" refers to the inclusion of the indicated active agent, such as a microRNA (miR) 302-367 cluster or a miR 302-367 cluster mimic and a histone deacetylase (HDAC) inhibitor, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient(s), however, other compounds may be included which are for stabilizing, preserving, etc. the formulation, but are not involved directly in the therapeutic effect of the indicated active ingredient. In some embodiments, components which facilitate the release of the active ingredient may be included. In some embodiments, the term "consisting" refers to a composition, which contains the active ingredient and a pharmaceutically acceptable carrier or excipient.

In one embodiment, a nucleic acid of the invention can be incorporated into pharmaceutical compositions. Such compositions typically include the therapeutic compounds and pharmaceutically acceptable carriers.

In one embodiment, "pharmaceutically acceptable carriers" include solvents, to dispersion media, coatings, antibacterial and antifungal agents, isotonic and absorption delaying agents, and the like, compatible with pharmaceutical administration. A pharmaceutical composition is formulated to be compatible with its intended route of administration. See, e.g., U.S. Pat. No. 6,756,196. Examples of routes of administration include parenteral, e.g., intravenous, intradermal, subcutaneous, oral (e.g., inhalation), is transdermal (topical), transmucosal, and rectal administration. In one embodiment, it is advantageous to formulate oral or parenteral compositions in dosage unit form for ease of administration and uniformity of dosage. In one embodiment, "dosage unit form" refers to physically discrete units suited as unitary dosages for the subject to be treated, each unit containing a predetermined quantity of an active compound calculated to produce the desired therapeutic effect in association with the required pharmaceutical carrier.

In one embodiment, the dosage required for treating a subject depends on the choice of the route of administration, the nature of the formulation, the nature of the subject's illness, the subject's size, weight, surface area, age, and sex, other drugs being administered, and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

In one embodiment, the miRNA of the compositions and methods of the present invention may be mature miRNA, while in another embodiment, the miRNA may be an miRNA precursor. In one embodiment, an miRNA precursor is a pre-miRNA, which in one embodiment, is subject to cleavage by an RNAse III type double stranded endonuclease called Dicer, resulting in one embodiment, in an imperfect miRNA:miRNA* duplex that in one embodiment, is around 20-25 nucleotides in size. This duplex, in one embodiment, contains the mature miRNA strand and its opposite complementary miRNA* strand.

In one embodiment, the invention provides a kit comprising: a somatic cell; an isolated nucleic acid comprising a microRNA (miR) 302-367 cluster or a miR 302-367 to cluster mimic; a histone deacetylase (HDAC) inhibitor; and instructions for producing an iPS cell from a somatic cell.

In one embodiment, the kit includes a transcription factor, e.g., a transcription factor or combination of transcription factors described herein, e.g., one or more of Oct4, Klf4, Sox2 or c-Myc or a nucleic acid encoding the same transcription factor. For example, the kit is can provide a vector, e.g., a plasmid or a viral vector, e.g., a retroviral, a lentiviral or an adenoviral vector, which can express mir302-367. In some embodiments, the transcription factor is fused to a tag, e.g., a GFP tag, a YFP tag or a RFP tag.

In one embodiment, the kit can include a component for the detection of a marker for iPS cells, e.g., for a marker described herein, e.g., a reagent for the detection of alkaline phosphatase (AP), NANOG, OCT4, SOX2, SSEA4, TRA-1-60 or TRA-1-81, e.g., an antibody against the marker or primers for a RT-PCR or PCR reaction, e.g., a semi-quantitative or quantitative RT-PCR or PCR reaction. Such markers can be used to evaluate whether an iPS cell has been produced. If the detection reagent is an antibody, it can be supplied in dry preparation, e.g., lyophilized, or in a solution. The antibody or other detection reagent can be linked to a label, e.g., a radiological, fluorescent or colorimetric label for use in detection. If the detection reagent is a primer, it can be supplied in dry preparation, e.g., lyophilized, or in a solution.

In one embodiment, the kit includes a component for karyotyping, e.g., a probe, a dye, a substrate, an enzyme, an antibody or other useful reagents for preparing a karyotype from a cell.

In another embodiment, the kit includes an iPS cell, e.g., an iPS cell derived from the same cell type as the somatic cell. In one embodiment, the iPS cell can be for use as a control.

In another embodiment, the kit includes informational materials, e.g., instructions, for use of two or more of the components included in the kit.

The kit can provide buffers e.g., reaction buffers, solvents, diluents, solutions, stabilizers, preservatives, media, cell lines, vectors, enzymes, secondary antibodies and other materials useful for practicing the methods e.g., a packaging cell line or a packaging vector for virus production, media for culturing iPS cells, or a secondary antibody used for Western to analysis or immunofluorescence staining.

All references mentioned herein are to be construed as being incorporated by reference in their entirety.

The following examples are presented in order to more fully illustrate the preferred embodiments of the invention. They should in no way be construed, however, as limiting the is broad scope of the invention. Methods for performing the experiments are well known to those skilled in the art.

EXAMPLES

Materials and Methods miR302-376 iPS Induction Experiments

The 690 bp fragment of the mouse or 644 bp of the human miR302-367 region, which is embedded in intron X of the Larp7 gene, was expressed using lentiviral vectors using constitutive or doxycycline inducible vectors. 2 mM valproic acid was added to enhance the stability and efficiency of the reprogramming.

Murine embryonic fibroblasts (MEFs) were infected with the lentivirus encoding the miR302-367 for 48 hours. A defined number of infected MEFs were plated on mitomycin inactivated feeder cells (either MEFs or STO cells) and the cells cultured in standard tissue culturing conditions (5% $CO_2$, 37° C.). Infected cells were visualized under phase contract or fluorescent microscopy.

Example 1

Transduction of Fibroblasts with miR302-367 in the Presence of Valproic Acid

The efficiency of colony formation in miR302-367 lentivirus-transduced fibroblast cells was more than 20% (50,000 MEFs transduced for all groups) by day 4 post viral transduction (FIG. 1) compared to an average of 0.1% for iPS cells generated using Oct3/4, Sox2, Klf4, and c-Myc (Takahashi et al., Cell 126:663-76, 2006; "4 factor"). Moreover, colonies were observed at day 4 in lentivirus-transduced fibroblast cells compared to after 7-14 days in 4 factor-generated iPS cells.

Example 2 miR302-367 iPS Cells Express Embryonic Stem Cell-Like Traits

Alkaline Phosphatase Staining

Cells were fixed with 4% paraformaldehyde (PFA) in phosphate buffered saline (PBS) at 4° C. over night. PFA was removed and cells washed twice with PBS+0.1% Tween-20 (PBT) for 5 min at room temperature (RT); in 50% methanol/50% PBT for 15 min at RT; and in 100% methanol twice for 15 min at RT. Cells were rinsed twice with PBT for 5 min at RT, equilibrated with NTMT (100 mM Tris pH 9.5, 100 mM NaCl, 50 mM MgCl2, 0.1% is Tween-20) with 3 rinses (5 min twice and 30 min) at RT. Cells were incubated in staining solution (168 mg 4-Nitroblue tetrazolium (NBT) and 84.5 mg 5-Bromo-4-chloro-8-indolilphosphate (BCIP) per 1 ml of NTMT for 40-120 min and then washed with PBT 3 times.

Immunohistochemistry

Tissue samples were fixed in 4% paraformaldehyde overnight at 4° C. The samples were washed sequentially with 1×PBS, methanol, isopropanol and tetrahydronaphthalene before embedded in paraffin wax. The embedded samples were then cut on a microtome at 7-10 μm thickness and mounted on clean TESPA-coated slides. Then, the slides were dewaxed with xylene and mounted under coverslips using mounting media (Richard Allan Scientific, Kalamazoo, Mich.) and stained by hematoxylin and eosin (H&E, Sigma) for morphological observation. Immunohistochemical staining kits were purchased from Imgenex (San Diego, Calif.). Processes for antibody dilution and immunostaining were performed according to the manufacturers' suggestions. Primary antibodies used included Nanog (1:500, Santa Cruz), Oct3/4 (1:500, Santa Cruz), and Sox2 (1:500, Santa Cruz). Fluorescent dye-labeled goat anti-rabbit or horse anti-mouse antibody was used as the secondary antibody (1:2,000, Invitrogen—Molecular Probes). Positive results were observed under a 100× microscope with whole field scanning and measured at 200× or 400× magnification for quantitative analysis by a Metamorph Imaging program (Nikon 80i and TE2000 microscopic quantitation systems). DAPI (Invitrogen) was used as a nuclear counterstain.

Figure 3:
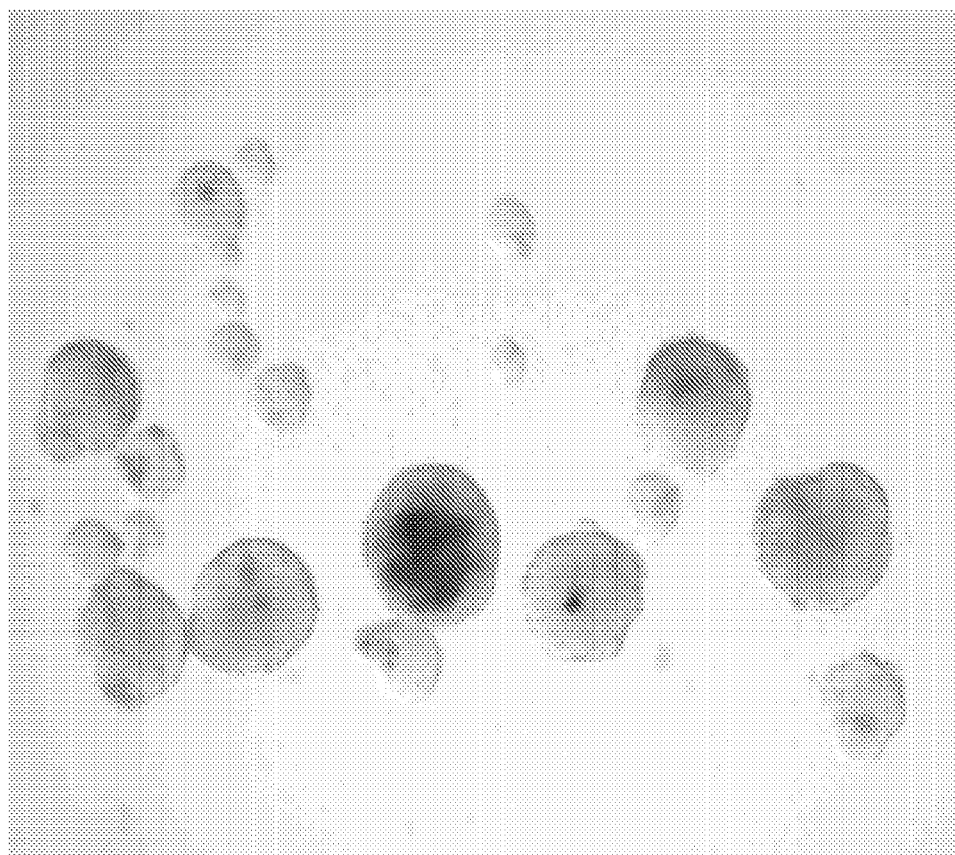
FIG. 3. miR302-367 iPS cells can generate embryoid bodies. miR302-367 iPS cells were aggregated as per standard protocols and differentiated for 10 days in suspension. The embryoid bodies formed were indistinguishable from ones formed by mouse embryonic stem cells.
Figure 4:
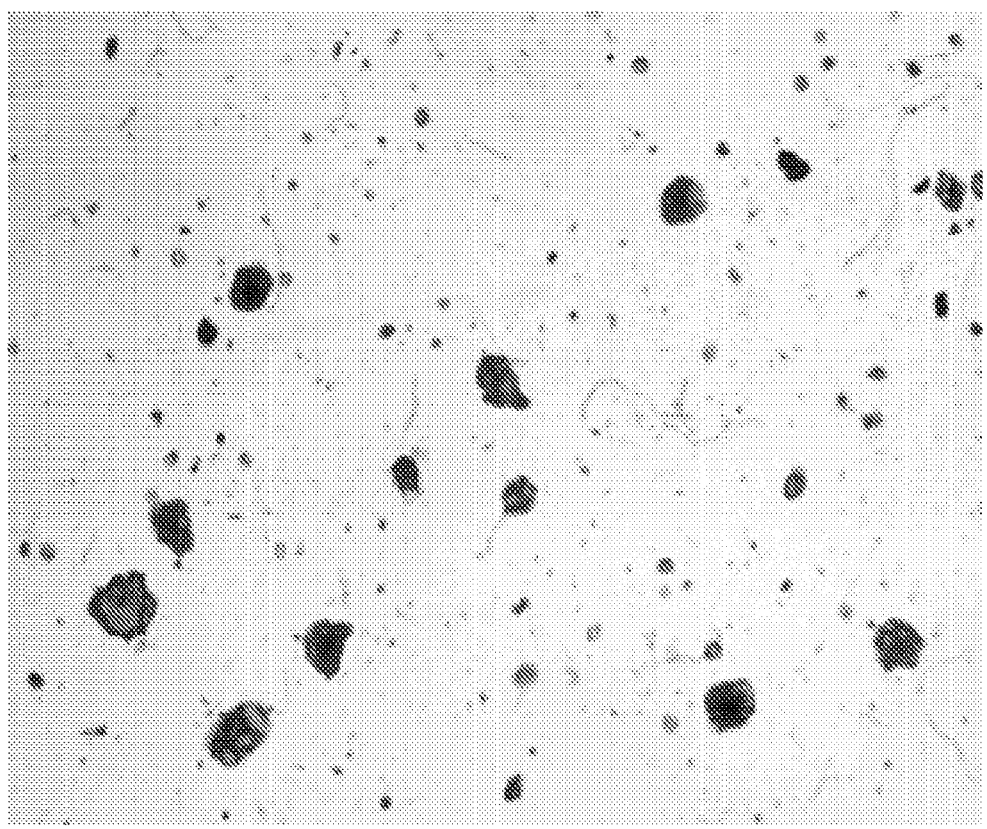
FIG. 4. miR302-367 iPS cells stain positive for alkaline phosphatase. Cells were cultured for 21 days after lentiviral infection.
Figure 5:
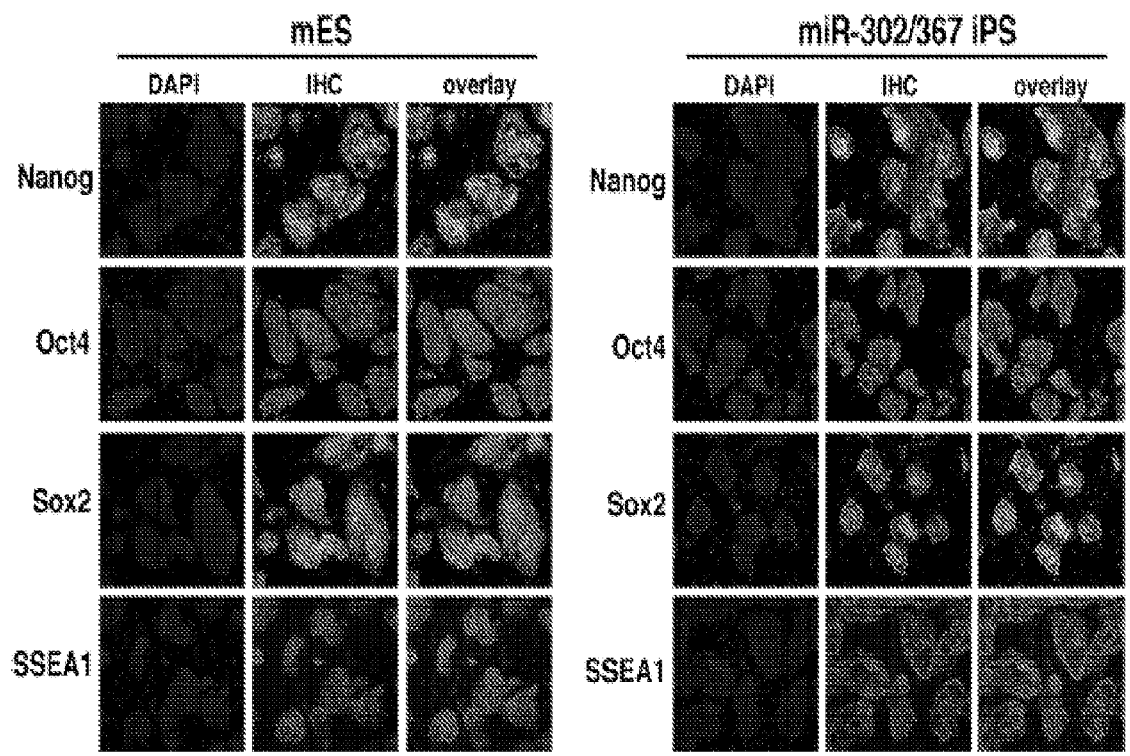
FIG. 5. miR302-367 iPS cells express markers of pluripotency. Expression of the pluripotent markers Nanog, Oct4, Sox2, and SSEA1 in both mouse embryonic stem cells and in miR302-367 iPS cells after 21 days of reprogramming.
Figure 6:
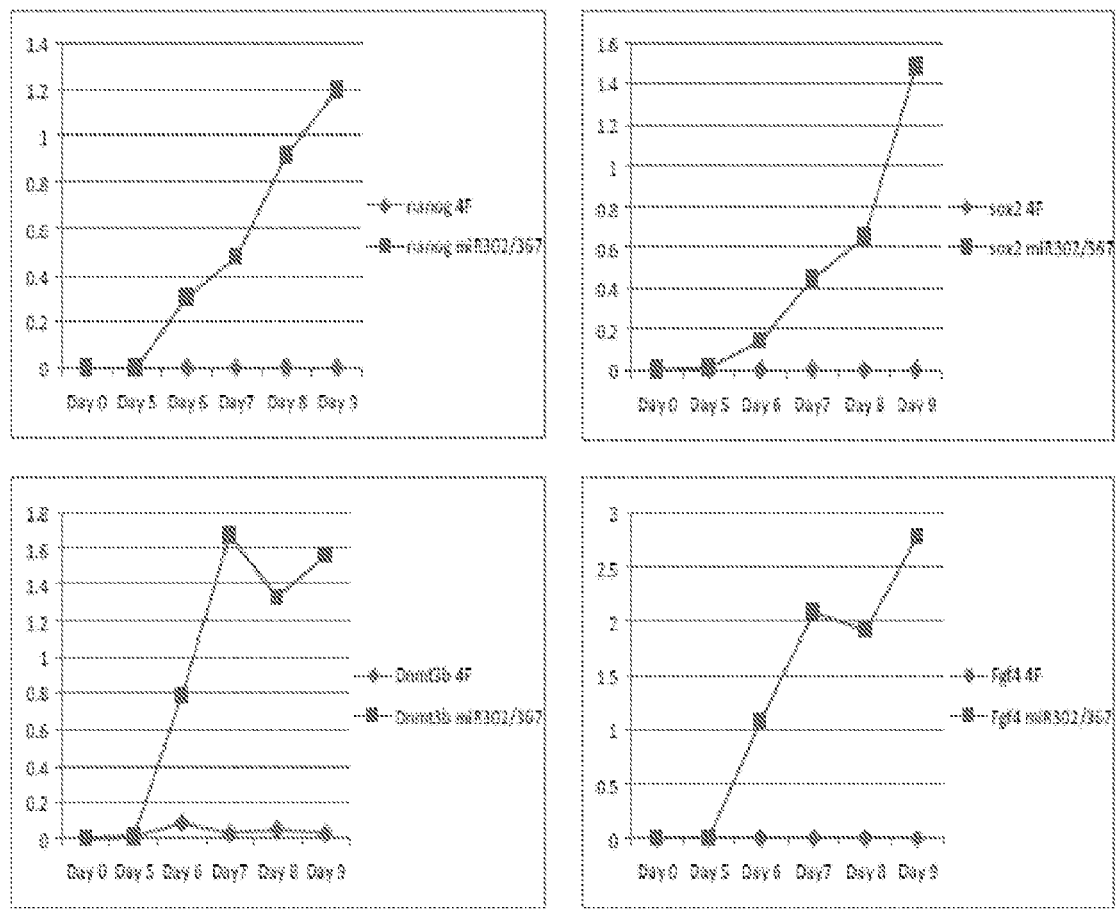
FIG. 6. Quantitative expression analysis (real time PCR) for pluripotential marker gene analysis.

Mir302-367 iPS cells were able to form compact colonies reminiscent of embryoid bodies (EBs) derived from mouse embryonic stem cells after 10 days in suspension (FIG. 3). Alkaline phosphatase is a stem cell membrane marker and elevated expression of this enzyme is associated with undifferentiated pluripotent stem cell. iPS cells express alkaline phosphatase 21 days after lentiviral infection (FIG. 4). iPS cells also express the pluripotent markers Nanog, Oct4, Sox2, and SSEA-1 in the nucleus after 21 days of reprogramming at the same level as do mouse embryonic stem cells (FIG. 5). In a series of quantitative expression analyses for pluripotential marker genes using real time PCR, Sox2, nanog, Fgf4, and Dnmt3b levels using the miR302/367 method of reprogramming fibroblasts are at least two orders of magnitude higher than the standard 4 factor (4F) method of reprogramming fibroblasts (FIG. 6).

Figure 2:
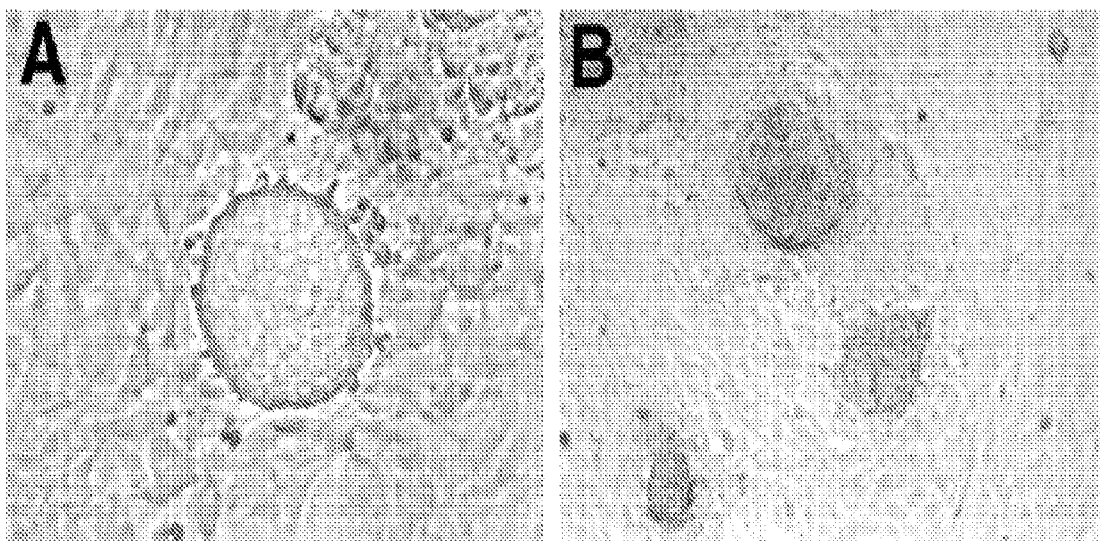
FIGS. 2A-B. miR302-367 iPS clones express Oct4 as noted by green fluorescent protein (GFP) expression from the endogenous Oct4 gene. MEFs made from the Oct4-GFP mouse line were transduced with the miR302-367 lentivirus, and pictures were taken 6 days after viral infection. Approximately 80% of colonies with an embryonic stem cell like morphology were GFP positive.

Similarly, MEFs isolated from the Oct4-GFP mouse line were transduced with the miR302-367 lentivirus GFP detected 6 days after viral infection. Approximately 80% of colonies with an embryonic stem cell like morphology expressed Oct4-GFP (FIG. 2).

Example 3 miR302-367 iPS Cells can Form Teratomas

In Vitro Molecular Guidance of the miR-Infected iPS Cell Differentiation

Xenograft implantation of the miR-infected iPS cells into the uterus or peritoneal cavity, but not other tissues, of a 6-wk-old female pseudopregnant, immunocompromised SCID-beige mouse could form a cyst full of teratoma-like primordial tissues. Immunocompromised nude mice provided an in vivo environment mimicking transplantation therapy. The pseudopregnant mice are made by intraperitoneally injection of 1 IU human menopausal gonadotrophin (HMG) for 2 d and then human chorionic gonadotrophin (hCG) for one more day. For in vitro molecular guidance into spermatogonia lineage, miR-infected iPS cells are maintained on polyornithine/laminin-coated dishes in DMEM/F12 (1:1; high glucose) medium supplemented with charcoal-stripped 10% FBS, 4 mM L-glutamine, 1 mM sodium pyruvate, 5 ng/mL activin, and 50 ng/mL dihydrotestosterone (DHT) for 12 h at 37° C. under 5% $CO_2$. Then the cells are trypsinized, washed with 1×PBS, and collected in four aliquots of chilled Matrigel (100 µL each) and one aliquots of 100 µL, 1×PBS. Immediately after that, cells are transplanted into the hind limb muscle, peritoneum, uterus, subcutaneous neck skin (with Matrigel), and tail vein (with PBS) of 6-wk-old athymic immunocompromised SCID-beige nude mice. The mice are anesthetized with diethyl ether during experimental processing.

One week later, spermatogonia-like cells are found only in the uterus area. For fibroblast differentiation, we follow the same procedure as shown above, except using regular phenol red-free DMEM medium supplemented with 10% FBS, 4 mM L-glutamine, 1 mM sodium pyruvate, 5 ng/mL noggin, and 100 ng/mL transforming growth factor-β1 (TGF-β1) for 6 h before xenotransplantation. Fibroblast-like cells are found in the uterus 1 wk later. For chondrocyte differentiation, we perform the same procedure as before but using regular to RPMI 1640 medium supplemented with 10% FBS, 4 mM L-glutamine, 1 mM sodium pyruvate, and 100 ng/mL bone morphogenetic protein 4 (BMP4) for 6 h. Chondrocyte-like cells are found only in the liver area.

These data confirm that miR302-367 iPS cells can make mesoderm, endoderm, and ectoderm cell lineages.

Figure 7:
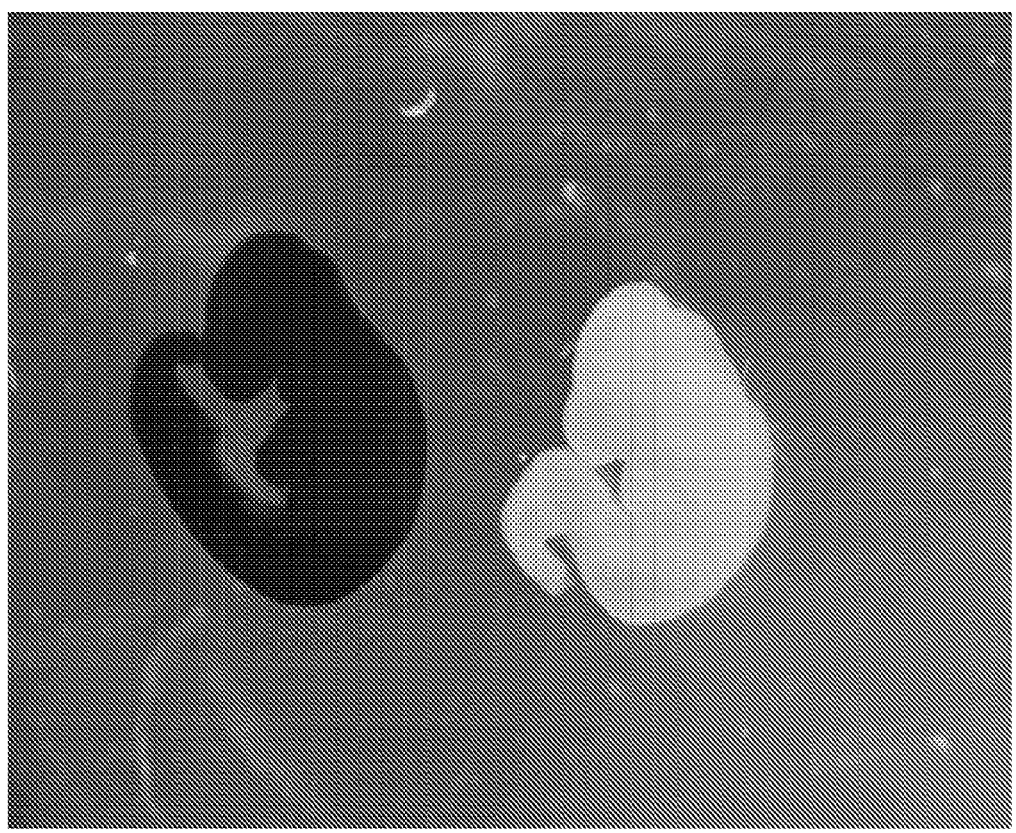
FIG. 7. miR302/367 iPS cells can generate all tissues within the developing vertebrate. Sample represents a total of 11 positive (blue) chimeras from a total of 24 embryos tested.

Example 4 miR302-367 iPS Cells Contribute to Multiple Cell Lineages within the Developing Embryo Using Chimeric Mice miR302/367 iPS cells were generated from MEFs from Rosa26 mice constitutively expressing lacZ. These cells were injected into E3.5 mouse blastocytes, and the embryos were harvested at E10.5 and stained for lacZ expression. The embryo that was generated from the Rosa26 miR302/367 iPS cells, is almost entirely blue (FIG. 7, left), indicating that miR302-367 iPS cells can generate all of the organs and tissues in vertebrates. The sample shown on the left represents 11 positive (blue) chimeras from a total of 24 embryos tested.

Somatic cells from embryos or adult mouse tissue are then harvested and the expression of reprogramming factors is re-induced, forming a secondary iPS cell population. A variety of tissue types are assessed for their reprogramming potential

Example 5

Transfection of Cells with miR302-367 Via Cell Transfection Methods and miR302-367 Mimics Electroporation, lipofection, gene guns, and microinjection are used to transfect cells as is known in the art with miR302-367.

Next, MEFs will be exposed to miR302-367 mimics ordered from Dharmacon allowing a viral and transfection free method for iPS cell generation. MEFs take up miR302-367 mimics quickly and at high efficiency and express embryonic stem cell markers, as described in Example 2 hereinabove.

Example 6

Directed Differentiation of miR302-367 iPS Cells into Cardiac Myocytes and Hematopoietic Cells The expression of cardiac marker genes in miR302-367 iPS cells is examined by semiquantitative and kinetic real time-PCR. miR302-367 iPS cells are cultured with BMP-2 (Puceat et al., 2008) and ascorbic acid (Takahashi et al., 2003). Semiquantitative RT-PCR demonstrates that all cardiac markers tested, such as GATA4, Nkx2.5, α-MHC, β-MHC, and ANF, are increased in BMP-2-treated miR302-367 iPS cells compared to vehicle-exposed to miR302-367 iPS cells, whereas the expression of Tie-2, which is expressed almost exclusively in endothelial cells, was not altered by BMP-2. These results suggest that miR302-367 iPS cells can differentiate into cardiac myocytes. In addition, immunoblot analysis is performed with antibodies against sarcomeric myosin and α-actinin. Treatment with BMP-2 increased the expression of these proteins in a dose-dependent manner compared is to untransfected miR302-367 iPS cells.

To create hematopoietic cells, miR302-367 iPS cells are exposed to mammalian hematopoietic stromal cells. At least some of the resulting cells are CD34+ (a standard marker for hematopoietic cells), or can form hematopoietic cell colony-forming units in methylcellulose culture.

Example 7

Highly Efficient miRNA Mediated Reprogramming of Somatic Cells to Induced Pluripotent Stem Cells One of the limitations of induced pluripotent stem cell reprogramming is the relative inefficiency of the process. We show that expression of the miR302/367 cluster rapidly and efficiently reprograms human and mouse somatic cells to an iPS state in the absence of Oct4/Sox2/Klf4/Myc. Reprogramming is two orders of magnitude more efficient than standard Oct4/Sox2/Klf4/Myc reprogramming miR302/367 iPS cells display similar characteristics as Oct4/Sox2/Klf4/Myc-iPS cells including the expression of pluripotent marker genes, teratoma formation, efficient generation of high percentage chimeric mice, and contribution to the germline. Within the miR302/367 cluster, miR367 expression is required for iPS cell reprogramming by activating Oct4 gene expression. Moreover, we demonstrate that suppression of Hdac2, which is specifically degraded by valproic acid, is required for miR302/367 mediated reprogramming.

In particular, we show that valproic acid (VPA) is required for reprogramming mouse fibroblasts by specifically degrading Hdac2 protein, a finding that is supported by the efficient reprogramming of Hdac2−/− fibroblasts in the absence of VPA. Thus, the expression of miR302/367 along with Hdac2 suppression allows for highly efficient iPS reprogramming without the expression of the known reprogramming factors.

These data demonstrate the potent and cooperative role of miRNAs and Hdac mediated pathways in pluripotent stem cell reprogramming.

Materials and Methods

Lentiviral Vector Construction

A mouse genomic DNA fragment comprising of miR302/367 or miR302a/b/c/d family of miRNA was amplified by PCR using primers listed in Table 1. The amplified fragment was cloned into Acc65I and XhoI restriction enzyme sites of pENTR1-A entry vector (Invitrogen) and verified by sequencing. The fragment was excised from the entry vector and ligated into BsrGI site of pLOVE destination vector (Blelloch et al., 2007) is resulting in pLOVE-mi R302/367 vector. The pLOVE-miR302a/b/c/d vector was generated in the same fashion but using a different 3' primer that excluded the miR367 sequence.

Cell Culture, Viral Production and Induction of Pluripotent Stem Cells

Mouse fibroblasts were isolated from Oct4-GFP, Rosa26-LacZ and Hdac2$^{flax/flax}$ embryos at E13.5 and cultured in fibroblast medium as described (Takahashi et al., 2007). Hdac2 was excised by infection of Hdac2$^{flax/flax}$ MEFs with adeno-cre virus. Human dermal fibroblast were cultured in DMEM/F12, 15% FBS, penicillin/streptomycin and L-glutamine. Viral particles were generated by transfection of plated 293T cells with pLOVE vectors encoding miR302/367, Oct4, Sox2, Klf4, or N-myc along with pMD.G and psPAX2 vectors as described (Blelloch et al., 2007). Supernatant from the transfected cells were collected every 24 hr for 48 hrs and titered. The titered viral suspension was mixed with 0.5 µl (0.1 of 10 µg/mL polybrene (American Bioanalytical, MA) per milliliter of viral suspension and used to infect fibroblasts. After viral infection, mouse fibroblast were cultured in mouse ES medium supplemented with or without valproic acid at a final concentration of 2 mM for the indicated length of time. Infected human fibroblast were culture in human ES medium as described (Huangfu et al., 2008a; Takahashi et al., 2007).

TABLE 1

Summary of clones tested for pluripotency. K clones were derived from human BJ foreskin fibroblasts. D clones were derived from dermal fibroblasts.

| Q-PCR mouse | IMMUNOSTAINING mouse | TERATOMA mouse | GERMLINE CONTRIBUTION mouse |
|---|---|---|---|
| C1 | C1 | C3 | C6 |
| C3 | C3 | C4 | C7 |
| C4 | C4 | C6 | C10 |
| C6 | C6 | C7 | |
| C7 | C7 | C10 | |
| C10 | C10 | | |
| human | human | human | |
| | K1 | K1 | K1 |
| | K2 | K2 | K2 |
| | K5 | K5 | K5 |
| | K7 | K7 | K7 |
| | | | D1 |

TABLE 1-continued

Summary of clones tested for pluripotency. K clones were derived from human BJ foreskin fibroblasts. D clones were derived from dermal fibroblasts.

| |
|---|
| D2 |
| D3 |

Immunostaining

Clones were washed twice in PBS (with $Mg^{2+}$ and $Ca^{2+}$) and fixed in 3.7% formaldehyde. Cells were permeabilized in 0.2% Nonidet P40 (Roche) and blocked in 10% goat serum. Cells were incubated in the following primary antibodies at 4° C. overnight: Oct3/4 (Santa Cruz Biotechnology), Sox2 (R&D Systems), Nanog (Abcam), SSEA1 and SSEA4 (Developmental Studies Hybridoma Bank), TRA-1-60 and TRA-1-81 (Millipore, Inc.), and to GFP (Clontech). Secondary antibodies are Alexa Fluor 488 and 568 (Invitrogen). The mounting medium used was Vectorshield with DAPI (Vector Laboratories). Alkaline phosphatase histochemical staining was performed using SIGMAFAST Fast Red TR/Naphtol AS-MX tablets following manufacturer's instructions (Sigma-Aldrich).

RNA Isolation, Quantitative RT-PCR, and Microarray Experiments

Total RNA was isolated using Trizol (Invitrogen). Two micrograms of RNA was used to synthesize cDNA using Superscript First Stand Synthesis Kit (Invitrogen). Real time PCR was performed using SYBR Green (Applied Biosystems) by 7900HT Fast Real Time PCR System (Applied Biosystems). Real time primer sequences are listed in Table 1. For microarray experiments, the Affymetrix Mouse Gene 1.0 ST arrays were used. Microarray data were analyzed using Robust Multichip Analysis (RMA) and Principal Component Analysis (PCA) and the Partek Genomics Suite v6.5.

Teratoma Formation and DNA Fingerprinting Analysis mR302/367 iPS cells were passaged twice on 0.1% gelatin coated plates for an hour to remove feeders. 5×10$^5$ cells were mixed with Matrigel and injected into each flank of NOD-SCID mice. Tumors were harvested at 4 weeks post-injection, fixed in 4% paraformaldehyde and embedded in paraffin. Sectioned tumors were stained for hematoxylin and eosin. For immunofluoresence staining, the primary antibodies were 13-111 tubulin (Abeam), MF-20 (Developmental Studies Hybridoma Bank) and E-cadherin (Cell Signaling). Genomic DNA from human miR302/367 iPS cell clones was used for DNA fingerprinting analysis (Cell Line Genetics, LLC, Madison, Wis.).

Generation of Mouse Chimeras with miR302/367 iPS Cell Clones miR302/367 iPS cells were generated using Rosa26-LacZ mouse embryonic fibroblasts (Friedrich and Soriano, 1991). The cells were passaged twice on 0.1% gelatin coated plates for an hour to remove feeders and injected into E3.5 C57BL/6 blastocysts. Embryos were harvested at E9.5 and E13.5 and stained for LacZ activity using previously is described methods (Shu et al., 2002). For germline contribution experiments, miR302/3671PS cell clones C6, C7, and C10, which were generated from Oct4-GFP MEFs, were used for blastocyst injection. Gonads were harvested from E13.5 and E15.5 embryos, visualized by fluorescence microscopy and then fixed and sectioned for GFP immunostaining. Embryos and tissues were embedded in paraffin and sectioned as described (Cohen et al., 2009; Shu et al., 2002). All three clones contributed to the germline.

Western Blots

Total cell lysates were prepared for Western blotting as previously described (Trivedi et al., 2008). Equal amounts of protein were resolved by SDS-PAGE and transferred to polyvinylidenedifluoride membranes. Membranes were incubated with Hdac1 antibody (1:1000 dilution, Cell Signaling), Hdac2 antibody (1:1000 dilution, Invitrogen) or Hdac3 antibody (1:1000 dilution, Sigma). Primary antibody binding was visualized by HRP-conjugated secondary antibody and detected by enhanced chemiluminescence (LumiGlo, Cell Signaling). For loading control, membranes were reprobed with primary antibody against GAPDH (1:2500 dilution, Abcam).

Proliferation Assays

Proliferation assays for MEFs were performed using the CellTiter 96 Aqueous One Solution Cell Proliferation kit (Promega, Inc.). 20 μl of CellTiter Reagent, which functions by being incorporated by viable cells into a colorimetric product that can be measured at 490 nm, was added to 100 μL of culture medium, incubated at 37° C. for and absorbance was measured at 490 nm at 1.5 hours, 2.5 hours, and 4.5 hours.

Generation of Conditional Hdac$^{flox/flox}$ Mice

The Hdac2p$^{flox/flox}$ allele was generated by flanking exon 2 with loxP recombination sites using the targeting vector depicted in FIG. 19A. Upon cre-mediated recombination, exon 2 is deleted and the resulting mRNA is out of frame with multiple early stop codons producing premature termination and loss of Hdac2 protein. This construct was electroporated into R1 ES cells; correctly targeted ES clones were to identified using Southern blot analysis (FIG. 19B) and used to generate high percentage chimeras and germline transmission of the Hdac2p$^{flox/flox}$ allele. Ubiquitous CMM-Cre transgenic mice were used to delete Hdac2 and to demonstrate the resulting loss of Hdac2 protein by Western blot analysis (FIG. 18C). Hdac2p$^{flox/flox}$ mice were crossed with Oct4-GFP knock-in mice (Lengner et al., 2007) to generate Hdac2p$^{flox/flox}$:Oct4-GFP mouse is embryonic fibroblasts which were treated with adenovirus expressing ere recombinase to delete Hdac2 for reprogramming experiments.

Results miR302/367 Reprograms Fibroblasts To an iPS Cell Phenotype

Figure 8:
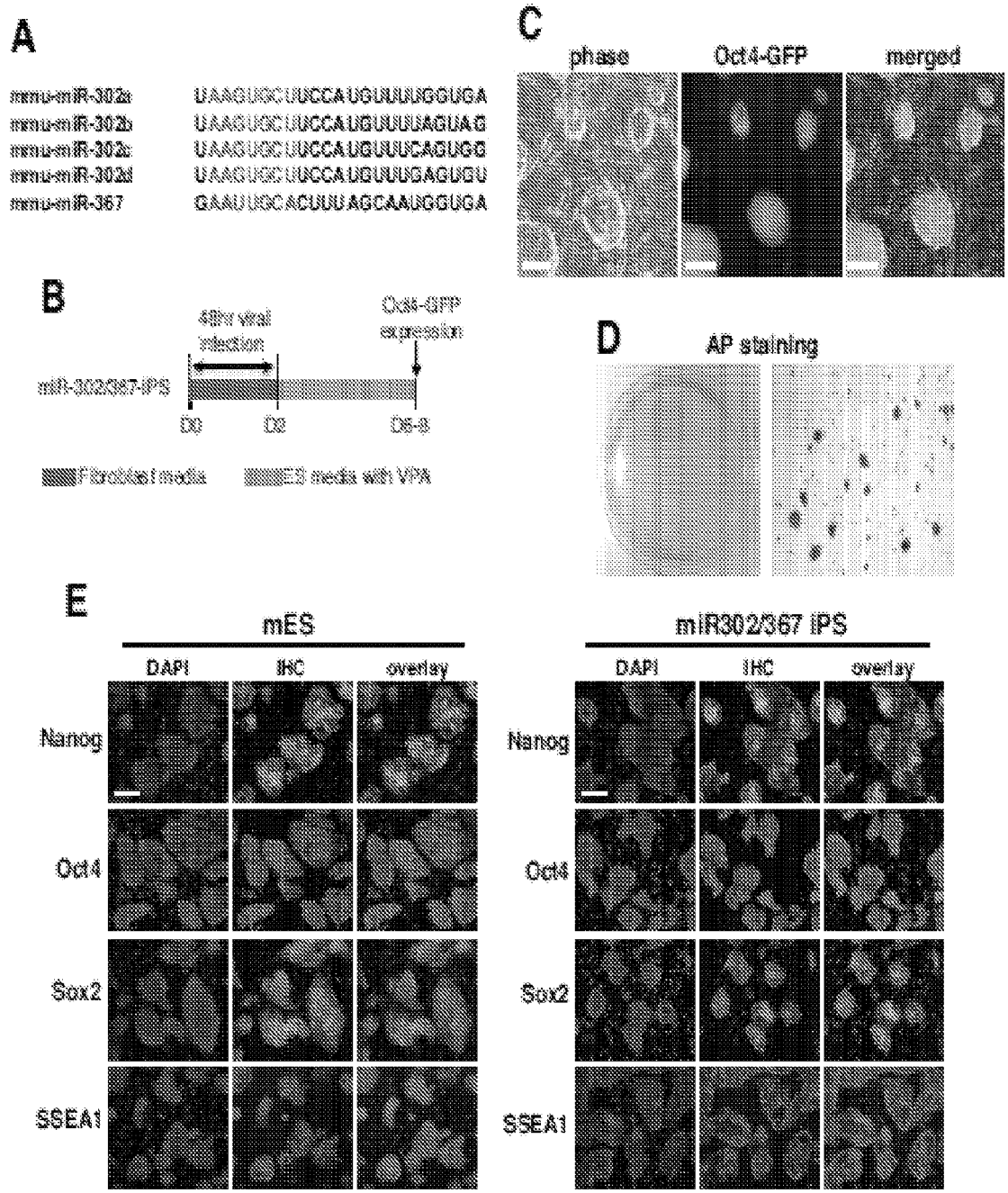
FIG. 8. miR302/367 can reprogram mouse fibroblasts to a pluripotent stem cell phenotype. (A) The sequences of the miR302/367 cluster showing the similarity between members of the miR302a/b/c/d (SEQ ID NOs: 5, 1, 3 and 7, respectively) subfamily. miR367 (SEQ ID NO: 10) has a different seed sequence than miR302a/b/c/d. (B) Schematic of viral expression protocol for miR302/367 iPS reprogramming with VPA. Day 0 is the start of viral transduction. (C) Oct4-GFP positive miR302/367 clones at seven days after starting viral transduction. (D) AP staining of a primary induction plate of miR302/367 iPS clones at eight days after starting viral transduction. (E) Immunostaining for Nanog, Oct4, Sox2, and SSEA1 in both mouse ES and primary induction samples of miR302/367 iPS cells at day 10 showing expression of pluripotent genes. Scale bars=100 µm.
Figure 10:
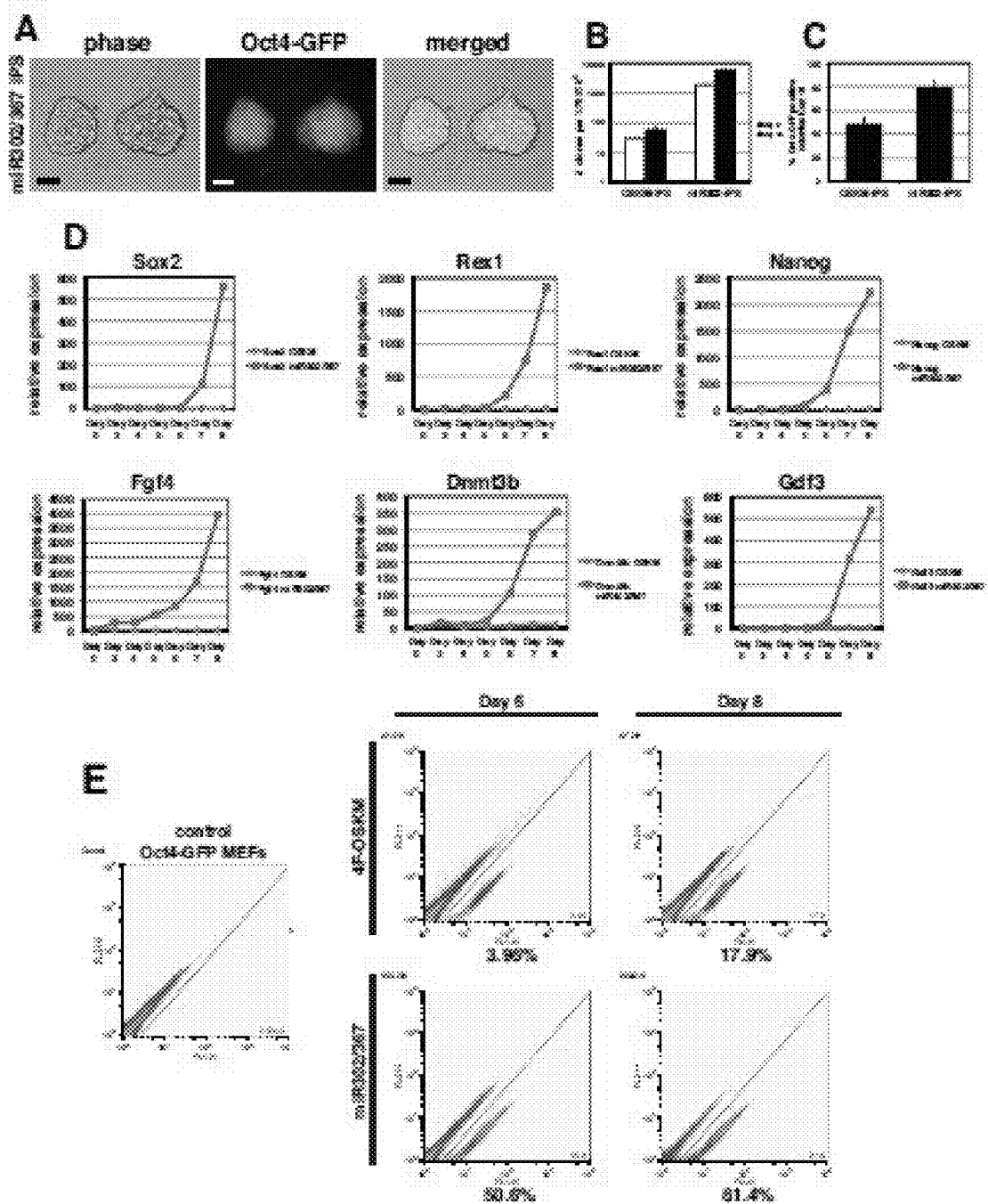
FIG. 10. miR302/367 plus VPA is two orders of magnitude more efficient that OSKM factors in iPS reprogramming of mouse fibroblasts. (A) miR302/367 iPS clones are readily observed 6-7 days after starting viral transduction and express high levels of Oct4-GFP while OSKM induced clones are not observed until 8-10 days, are very rare, and do not express significant levels of GFP from the Oct4 locus. (B) Counts of clones with ES like morphology from transduction of $1.75 \times 10^4$ Oct4-GFP MEFs with equivalent amounts of either OSKM or miR302/367 virus at eight and ten days after viral transduction. Data are the average of three assays±S.E.M. (C) Percentage of Oct4-GFP positive clones ten days after viral transduction with OSKM or miR302/367. Data are the average of three assays±S.E.M. (D) Q-PCR of the indicated pluripotent factors comparing OSKM versus miR302/367 during the first eight days after viral transduction. (E) FACS analysis of miR302/367 reprogrammed Oct4-GFP MEFs compared to OSKM reprogrammed MEFs at six and eight days post-viral transduction. Scale bars=50 µm.

Pervious studies have shown that the miR302/367 cluster is comprised of five miRNAs, four of which, miR302a/b/c/d, have an identical seed sequences. The miR302/367 cluster is located in intron 8 of the Larp7 gene on chromosome 3 and is transcribed as a single polycistronic primary transcript (Card et al., 2008). The sequence of the miR302/367 miRNAs are highly conserved across species (Card et al., 2008; Rosa et al., 2009). To determine whether expression of miR302/367 could reprogram somatic cells, we generated a lentiviral vector which expressed the 690 bp region encoding the mouse miR302/367 sequences and used it to transfect mouse embryonic fibroblasts (MEFs) derived from the Oct4-GFP mouse line ((Lengner et al., 2007) and FIG. 8B). We included the Hdac inhibitor VPA in these experiments as this has been shown to enhance iPS reprogramming (Huangfu et al., 2008a). Surprisingly, we observed clones derived from miR302/367 transduced MEFs within 6-8 days after the start of viral infection that had already assumed an ES cell like morphology (FIGS. 8C and 10A). Most of these clones were Oct4-GFP positive and alkaline phosphatase positive (FIGS. 8C and D). These clones also expressed Nanog, Sox2, and SSEA1 (FIG. 8E). In comparison, parallel expression of OSKM expressing viruses in addition to VPA did not result in any visible clones until at least 8-10 days after starting viral transduction (FIG. 10). Use of a polycistronic virus did not alter the timing or overall number of colonies generated by OSKM expression (Sommer et al., 2009). Moreover, in the absence of VPA, miR302/367 was unable to reprogram MEFs efficiently.

Figure 9:
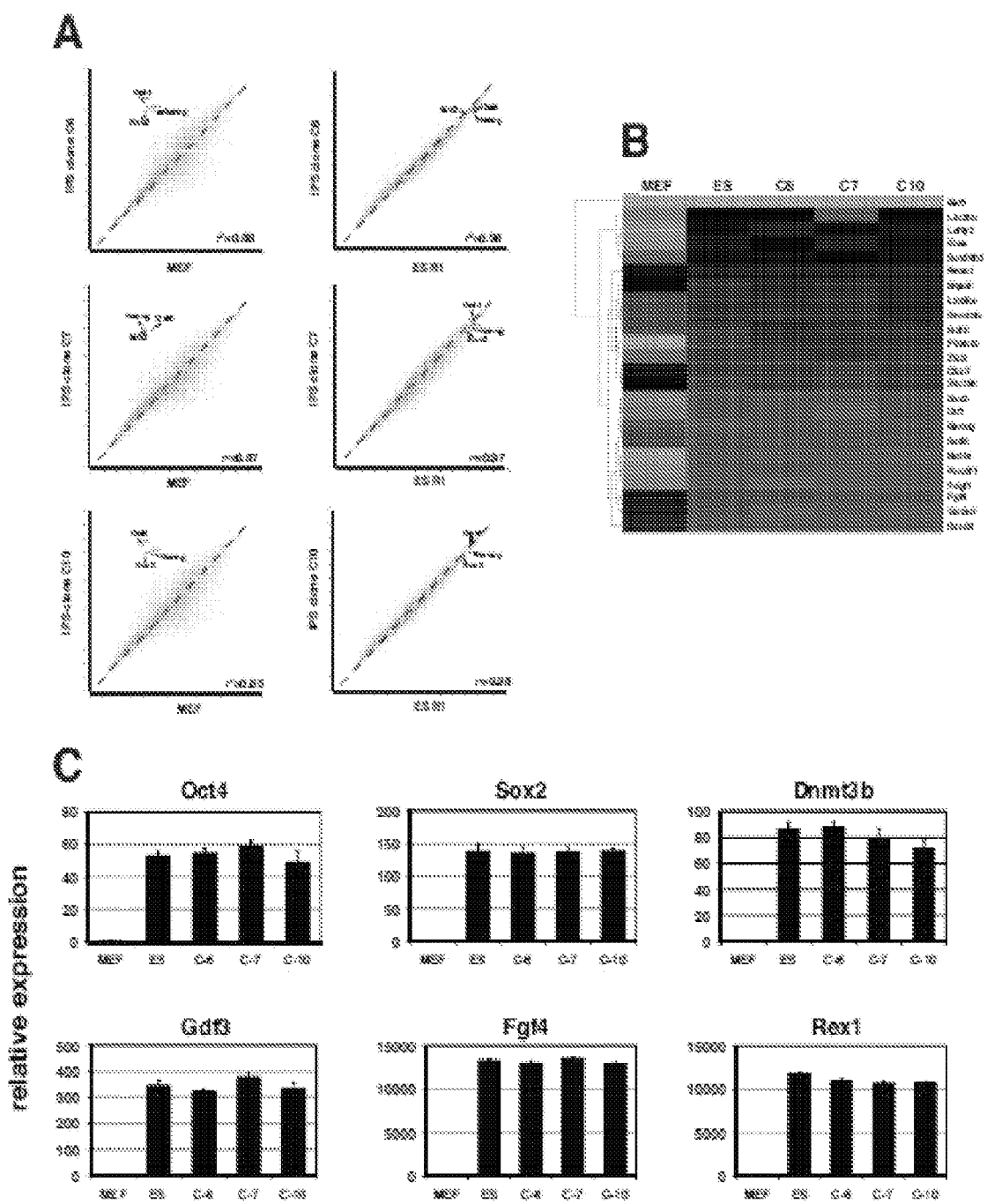
FIG. 9. miR302/367 iPSC clones have a similar expression profile as mouse ES cells. (A) Microarray experiments were used to show the similarity between miR302/367 iPS cell clones C6, C7, and C10 at passage 15 and the mouse ES cell line R1. (B) Heatmap of pluripotent gene expression of mouse ES cell line R1 and miR302/367 iPS cell clones C6, C7, and C10 from experiment in A. (C) Q-PCR of pluripotent gene expression of miR302/367 iPS cell clones C6, C7, and C10 at and mouse ES cell line R1.
Figure 16:
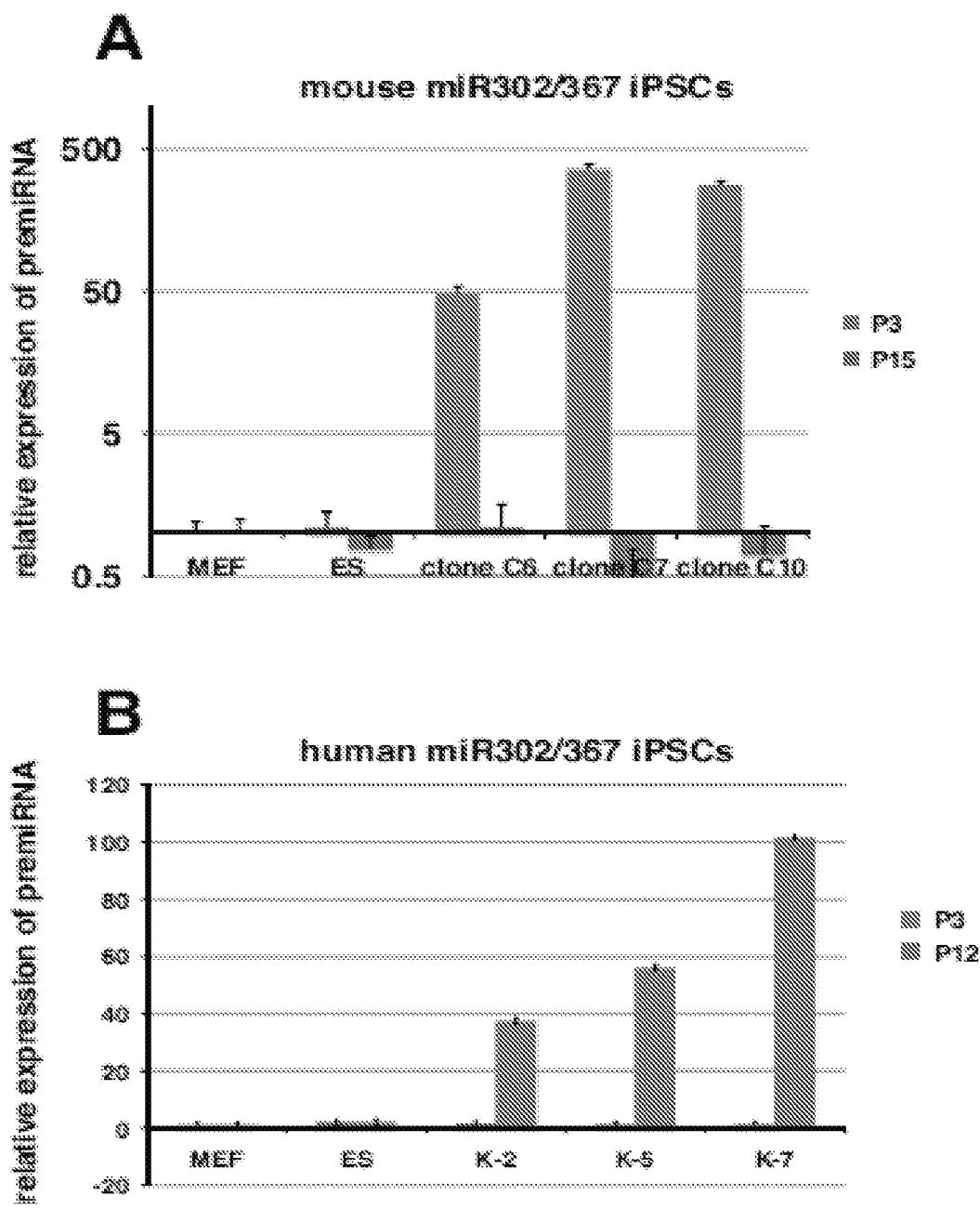
FIG. 16. Expression of the miR302/367 pre-miRNA is extinguished in late passage miR302/367 iPS cell clones. Q-PCR for the pre-miRNA for miR302/367 virally expressed sequences in MEFs, mouse ES line R1, and miR302/367 clones C6, C7, and C10 at passage 3 and 15 (A) and the same in human clones K2, K5, and K7 at passages 3 and 12 (B). Primers used are listed in Table 1.

We further characterized the miR302/367 generated iPS clones by microarray analysis for their similarity at the global gene expression level to the mouse ES cell line R1. We used clones at passage 15 for these analyses. These data show a very high degree of correlation with global gene expression in the R1 ES cell line (FIGS. 9A and B). These clones to lacked integration of any of the OSKM factors that we use as controls but did contain viral integration of the miR302/367 lentivirus into the genome (FIG. 15). miR302/367 iPS clones that have been passaged serially maintain their ES like morphology and Q-PCR shows that they exhibit identical expression of pluripotent genes as mouse ES cells (FIG. 9C). Moreover, the miR302/367 lentivirus is silenced at later passages (FIG. 16). These results indicate that is expression of miR302/367 in addition to VPA was able to reprogram mouse MEFs to an iPS cell state without expression of other previously described pluripotent factors.

miR302/367 Reprogramming is More Efficient Than OSKM Reprogramming

The rapid appearance of miR302/367 reprogrammed iPS cells indicated that expression of these miRNAs improved the temporal kinetics of reprogramming. To test this hypothesis, we expressed in parallel miR302/367 and the OSKM genes using an identical number of starting MEFs and viral titer. VPA was included in both OSKM as well as miR302/367 reprogramming experiments. Previous studies have demonstrated that using the OSKM factors, an average colony forming reprogramming efficiency of 0.2-0.8% is observed (Huangfu et al., 2008a). Using miR302/367, we consistently observe Oct4-GFP positive clones seven days after starting viral transduction, which is sooner than cells transduced in parallel with the OSKM factors (FIG. 10A). By counting the number of clones with ES like morphology at eight and ten days after starting viral transduction, we show that expression of miR302/367 produces two orders of magnitude more iPS clones than when the OSKM factors are used (FIG. 10B). At day 10, 79.8% of miR302/367 iPS clones exhibited robust expression of Oct4-GFP which is greater than clones expressing the OSKM factors, of which only approximately 50% express Oct4-GFP (FIG. 10C).

To better quantify this increase in iPS reprogramming efficiency, we performed quantitative real time PCR (Q-PCR) for pluripotent marker genes during the first eight days of the reprogramming process on primary induction plates. The experiment used the same number of starting MEFs and viral titer for infection. These data show that while cells transduced with the OSKM factors expressed only very low levels of pluripotent marker genes during this time period, miR302/367 transduced cells expressed all of the genes examined at robust levels by day 8 (FIG. 10D). The numbers of clones were such that after 8-10 days, the plates containing the miR302/367 iPS clones became overcrowded resulting in decreased cell viability unless they were isolated and expanded. We also assessed the to efficiency of reprogramming by miR302/367 using fluorescent activated cell sorting (FACS) for expression of GFP from the Oct4 locus in Oct4-GFP MEFs (Lengner et al., 2007). OSKM reprogrammed MEFs do show Oct4-GFP expression at both six and eight days of the reprogramming process with up to 17% of cells expressing GFP by day eight which is in the same range as previously reported (FIG. 10E and (Huangfu et al., 2008a)).

Figure 11:
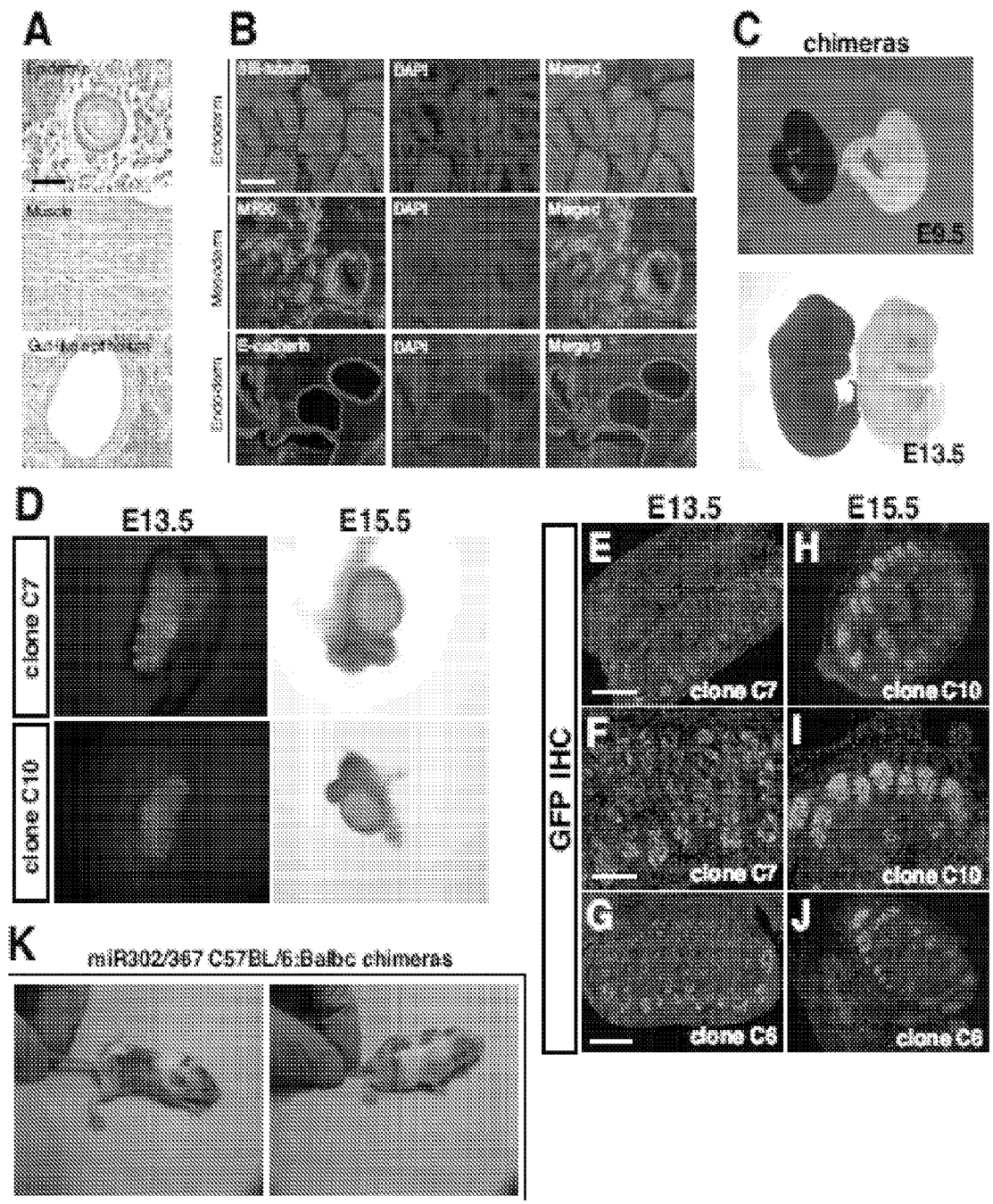
FIG. 11. miR302/367 iPS cells can generate derivatives of mesoderm, endoderm, and ectoderm and contribute to the germline of mice. (A) Hematoxylin and eosin staining of teratomas derived from miR302/367 iPS cell clones showing skin epidermal-like structures, muscle, and gut-like epithelium. These data are representative of five different to miR302/367 iPS cell clones which were injected and all produced teratomas. (B) Immunostaining of miR302/367 iPS derived teratoma tissues showing expressing of β111-tubulin positive neural epithelium, MF20 positive striated muscle, and E-cadherin positive endodermal cells. (C) miR302/367 iPS clones can generate all tissues within the developing embryo as shown by lacZ histochemical staining of high percentage chimeric embryos is derived from Rosa26-miR302/367 iPS clones at both E9.5 and E13.5. (D) Both whole mount fluorescence (D) and immunostaining for Oct4-GFP protein expression (E-J) show high-level contribution of miR302/367 iPS cell clones to the germline within the gonads of recipient mice. The data are representative of three clones (C6, C7, C10) which were injected into blastocysts and all three contributed to the germline. (K) miR302/367 iPSCs generated from C57BL/6 MEFs generate high percentage postnatal chimeras as noted by coat color. Scale bars: A=100 µm and B, D, G, H, J=150 µm, F and 1=100 µm.
Figure 17:
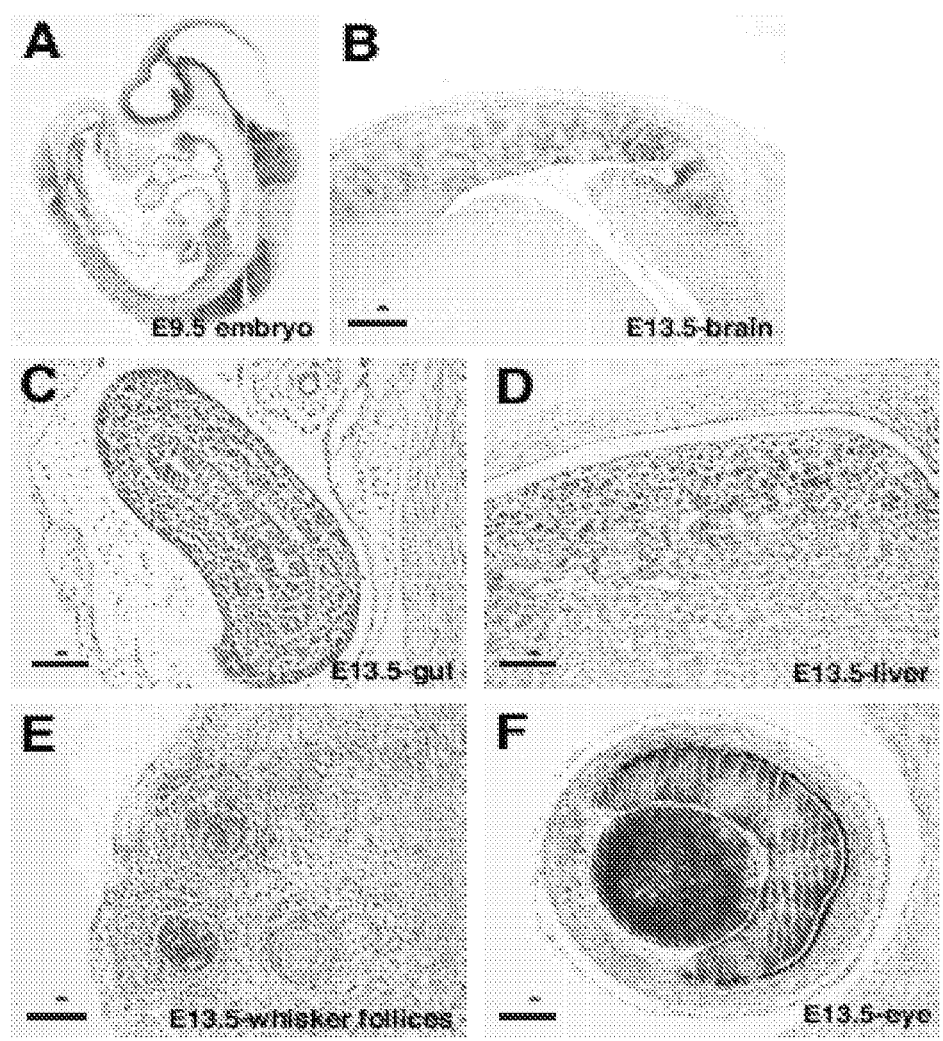
FIG. 17. Contribution of miR302/367 iPS cells to mouse tissues. miR302/367 iPS clones were injected into blastocysts and embryos were harvested at either E9.5 (A) or E13.5 (B) and histochemically stained for β-galactosidase expression. Expression is observed throughout the developing embryo at E9.5 (A). Representative lacZ staining in brain (B), gut (C), liver (D), whisker follicles (E), and eye (F) at E13.5. Scale bars=150 μm.

However, is miR302/367 is able to activate Oct4-GFP expression in up to 80% of MEFs after eight days of reprogramming (FIG. 10E). These data support the conclusion that miR302/367 is able to reprogram fibroblasts to a pluripotent state up to two-orders of magnitude more efficiently than OSKM factors.

miR302/367 iPS Cells Can Generate Derivatives of Mesoderm, Endoderm, and Ectoderm in Teratomas, Generate Adult Chimeras, and Contribute to the Mouse Germline To more fully characterize the pluripotent characteristics of miR302/367 iPS cells, we generated teratomas in immune deficient mice with multiple miR302/367 iPS clones. miR302/367 iPS derived teratomas formed readily and exhibited tissues representing all three germ layers as noted by structures resembling muscle fibers, keratinized epidermal cells, and luminal structures lined with gut-like epithelium (FIG. 11A). Supporting these morphological findings, neural epithelial-like structures were positive for pill-tubulin expression, muscle-like structures were positive for myosin heavy chain expression, and gut-like epithelium was positive for E-cadherin expression (FIG. 11B). A more stringent assay for pluripotency is determining whether miR302/367 iPS cells can generate tissues within the developing embryo using chimeric embryo analysis. Therefore, we generated miR302/367 iPS clones from MEFs made from the Rosa26lacZ mouse line which expresses β-galactosidase ubiquitously (Friedrich and Soriano, 1991). Injection of these miR302/367 iPS clones generated high percentage chimeras in more than 50% of the injected embryos (FIG. 11C). Most of these chimeras exhibited 80-95% contribution from miR302/367 iPS cells to all tissues examined (FIG. 11C and FIG. 17).

Figure 12:
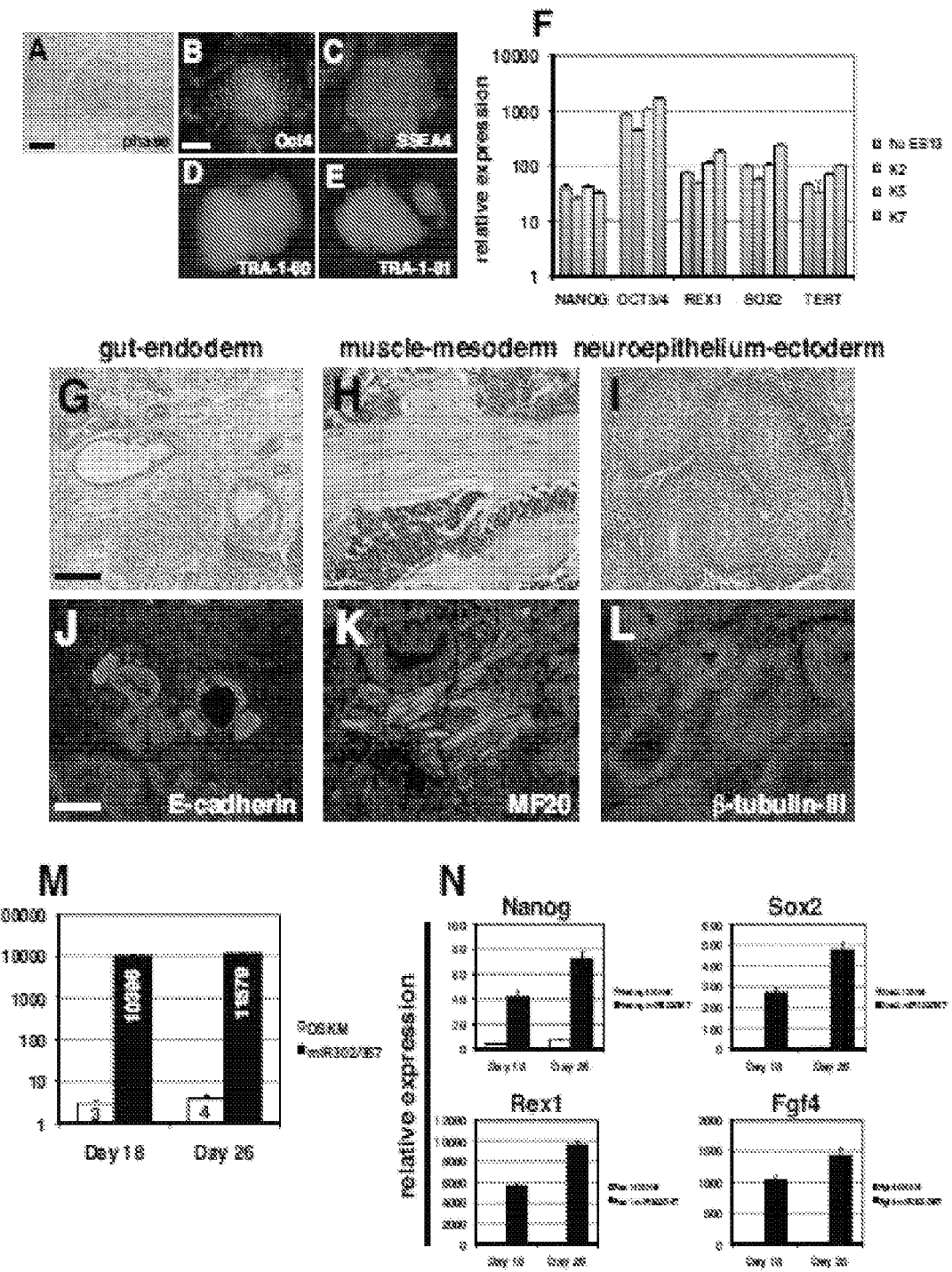
FIG. 12. miR302/367 reprograms human fibroblasts to a pluripotent state more efficiently than OSKM factors. (A-E) Colony morphology and OCT4, SSEA4, TRA-1-60, and TRA-1-81 immunostaining of miR302/367 reprogrammed human fibroblasts. (F) Q-PCR of pluripotent stem cell marker genes in three different miR302/367 reprogrammed human fibroblast lines as compared to the human ES line HUES 13. (G-I) Hematoxylin and eosin staining of teratomas derived from miR302/367 human iPS cell clones showing endoderm (gut), mesoderm (muscle), and ectoderm (neural epithelium) like structures. These data represent the results from seven human miR302/367 iPS cell clones. (J-L) Immunostaining of miR302/367 human iPS cell derived teratoma tissues showing expressing of E-cadherin positive endodermal cells, MF20 positive striated muscle, and βIII-tubulin positive neural epithelium. (M) Efficiency of miR302/367 reprogramming in human foreskin fibroblasts by colony counts of clones with human ES like morphology at 18 and 26 days post-viral transduction. Data are the average of three assays±S.E.M. (N) Q-PCR of pluripotent gene expression in miR302/367 reprogrammed human foreskin fibroblasts at 18 and 26 days post-viral transduction. Data are the average of three assays±S.E.M. Scale bars: A-E=50 μm, G-L=150 μm.

To test whether miR302/367 iPS cells could contribute to the germline of mice, we injected three different mouse miR302/367 iPS clones derived from Oct4-GFP MEFs. Mouse gonads were collected at E13.5 and E15.5 and visualized both by whole mount fluorescence and then fixed and sectioned for immunostaining for GFP expression. All three clones contributed efficiently to germ cells in the gonads of chimeric mice (FIG. 11D-J). Moreover, miR302/367 iPS clones generated from C57BL/6 MEFs can generate high percentage postnatal chimeras (FIG. 11K). Thus, miR302/367 iPS clones are pluripotent, are competent to to generate all three germ layers, and contribute efficiently to the germline of mice. A summary of mouse clones tested for pluripotency is found in Table 1.

miR302/367 can Reprogram Human Fibroblasts to a Pluripotent State More Efficiently than OSKM Factors To assess whether miR302/367 can reprogram human fibroblasts, we transduced is human foreskin and dermal fibroblasts with the miR302/367 lentivirus. Within 12-14 days, we observed clones with the classic human ES cell morphology (FIG. 12A). Immunostaining of these clones showed they expressed OCT4, SSEA4, TRA-1-60, and TRA-1-81 (FIG. 12 B-E). Q-PCR using three different miR302/367 hiPS cell clones shows that they all express pluripotent markers at levels equivalent to the hES cell line HUES 13 (FIG. 12F). We reprogrammed the human foreskin fibroblast cell line BJ and performed DNA fingerprinting to show that clones from miR302/367 reprogramming are derived from the original parental BJ line (FIG. 18). Moreover, these human clones did not contain any integrants of the OSKM viruses and the miR302/367 virus was silenced in later passages (FIGS. 15 and 16). Interestingly, VPA was not required for reprogramming human fibroblasts and its addition did not affect the efficiency of reprogramming (see below). Teratomas were generated from seven different miR302/367 hiPS clones and all exhibited formation of mesoderm, endoderm, and ectoderm (FIG. 12G-L). A summary of human clones tested for pluripotency is found in Table 1.

We next assessed whether there was an increase in human reprogramming efficiency similar to what we observed in MEFs. Starting with the same number of human foreskin fibroblasts and OSKM and miR302/367 viral titers, the number of colonies with ES like morphology formed at 18 and 26 days after starting viral transduction is two-orders of magnitude greater for miR302/367 than when using OSKM expression (FIG. 12M). Based on the cell counts, approximately 10% of human fibroblasts used for viral transduction produce iPS cell clones (FIG. 12K). Q-PCR from primary induction plates also reveals a dramatic increase in pluripotent gene expression in miR302/367 expressing versus OSKM expressing human foreskin fibroblasts (FIG. 12N). These data show that miR302/367 can reprogram human as well as mouse fibroblasts to an iPS cell state with greatly increased efficiency.

miR367 Expression is Required For miR302/367 iPS Reprogramming

Figure 13:
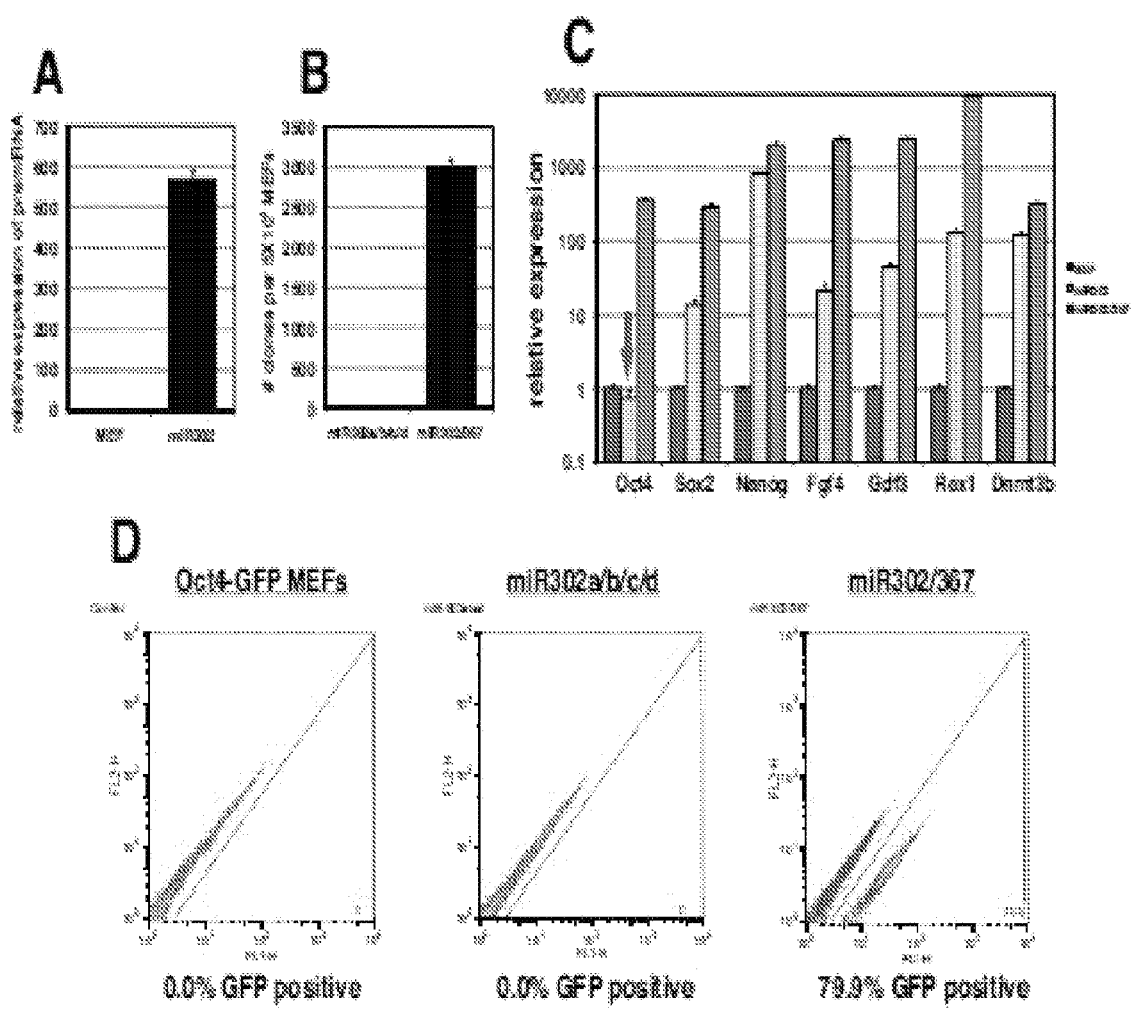
FIG. 13. miR367 expression is required for miR302/367 iPS cell reprogramming (A) The miR302a/b/c/d pre-miRNA is expressed at high levels in transduced MEFs. (B) Number of colonies generated after 10 days of miR302a/b/c/d or miR302/367 expression. Data are the average of four assays±S.E.M. (C) Pluripotent gene expression from primary induction plates eights days after viral induction of miR302a/b/c/d or miR302/367 viruses. Note lack of Oct4 gene expression in miR302a/b/c/d expressing cells (red arrow). Data are the average of three assays±S.E.M. (D) FACS analysis of Oct4-GFP MEFs eight days after transduction with either miR302a/b/c/d or miR302/367 viruses.

The miR302/367 cluster contains five different miRNAs, miR302a/b/c/d and miR367. All are expressed from a common promoter located in intron 8 of the Larp7 gene to (Card et al., 2008). miR302a/b/c/d all share a common seed sequence indicating that they target a similar set of mRNAs and thus may act redundantly (FIG. 8A). However, miR367 has a different seed sequence and thus may target a different set of mRNAs (FIG. 8A). Therefore, we tested whether miR367 expression is required for miR302/367 iPS cell reprogramming. Using a lentivirus lacking the miR367 sequence, we infected Oct4-GFP is MEFs alongside the miR302/367 lentivirus and assessed pluripotent reprogramming by colony counts, Q-PCR and FACS analysis. The miR302a/b/c/d virus lacking miR367 is expressed at high levels in MEFs (FIG. 13A). However, miR302a/b/c/d did not generate any iPS cell colonies when expressed in MEFs at day 10 of reprogramming (FIG. 13B). Continued culture for up to three weeks did not result in formation of any iPS cell colonies from miR302a/b/c/d transduced MEFs. Moreover, expression of miR367 alone did not reprogram fibroblasts. Q-PCR of primary induction plates eight days after viral transduction shows that several important pluripotent genes were expressed at lower levels in miR302a/b/c/d transduced MEFs versus miR302/367 transduced MEFs (FIG. 13C). Importantly, Oct4 expression is not observed at detectable levels in response to miR302a/b/c/d expression (FIG. 13C, arrow). Using FACS analysis and Oct4-GFP MEFs, we show that there is no induction of Oct4 gene expression when expressing miR302a/b/c/d without miR367 while miR302/367 expression induces robust Oct4-GFP expression by day eight (FIG. 13D). These data show that without miR367 expression, miR302a/b/c/d expression was unable to reprogram mouse MEFs and that this correlated with a lack of induction of Oct4 gene expression. Thus, the coordinated action of the miR302a/b/c/d family along with miR367 is required for iPS cell reprogramming.

Low Levels of Hdac2 Permit miR302/367 Reprogramming

Figure 14:
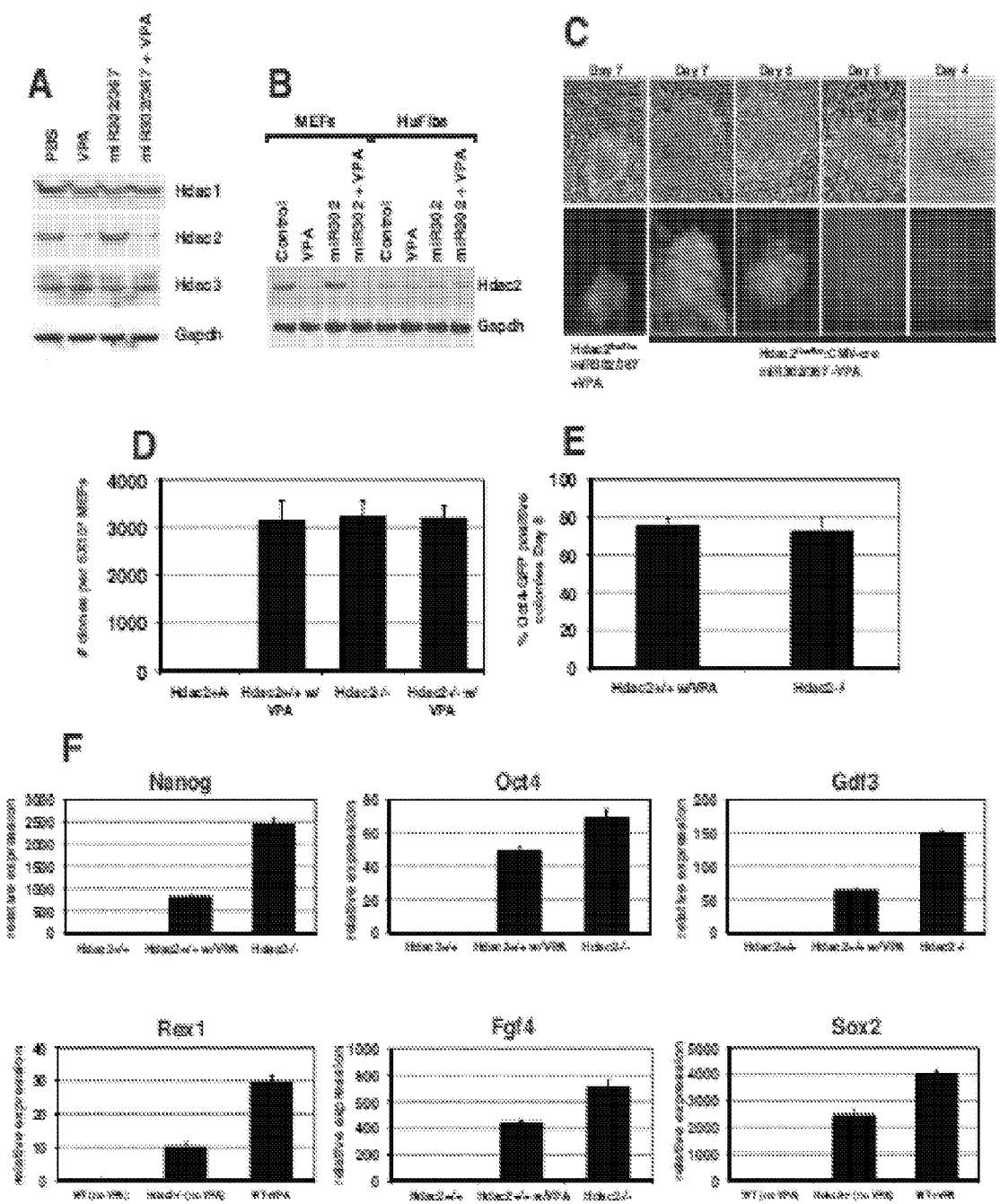
FIG. 14. VPA specifically degrades Hdac2 protein and suppression of Hdac2 is required for iPS reprogramming by miR302/367. (A) VPA specifically degrades Hdac2 but is not Hdac1 or Hdac3 proteins. Expression of miR302/367 alone did not have any affect on Hdac1, -2, or -3 protein levels. (B) Human foreskin fibroblasts express much lower levels of Hdac2 than MEFs. (C) Hdac2-/- MEFs start to reprogram between six and seven days post viral transduction which is similar to wild-type MEFs treated with VPA. (D) Number of clones generated with Hdac2-/- MEFs in the absence of VPA is similar to Hdac2+/+ MEFs with VPA at eight days post-viral transduction. Hdac2+/+ MEFs without VPA treatment did not generate any viable clones and VPA addition to Hdac2-/- MEFs did not increase the number of clones generated. (E) Percentage of Oct4-GFP positive clones is similar for Hdac2+/+ MEFs with VPA treatment and Hdac2-/-MEFs without VPA treatment at eight days post-viral transduction. (F) Q-PCR for pluripotent stem cell marker genes shows enhanced expression of pluripotency markers at day eight of reprogramming by miR302/367 in wild-type and Hdac2-/- MEFs versus Hdac2+/+ MEFs without VPA treatment. Data are the average of three assays±S.E.M.

Recent evidence has pointed to an important role for chromatin remodeling factors in regulating the ES cell pluripotent state (Lagarkova et al., 2010; Mali et al., 2010). Previous data has shown that VPA, a known Hdac inhibitor, enhances OSKM reprogramming indicating an important role for Hdac mediated chromatin remodeling in iPS reprogramming (Huangfu et al., 2008a). We initially found that in the absence of VPA, miR302/367 was unable to efficiently reprogram MEFs to iPS cells and of the few clones that did develop, none survived clonal replating (FIGS. 14D and F). Interestingly, VPA was not necessary for reprogramming of human foreskin or dermal fibroblasts (FIG. 12). VPA has been reported to specifically degrade Hdac2 protein (Kramer et al., 2003). Therefore, we assessed whether expression of class I Hdacs was altered by miR302/367 or VPA treatment by performing Western blots for Hdac1, 2, and 3 expression during miR302/367 mediated reprogramming. While Hdac1 and Hdac3 expression levels were unchanged in all conditions, VPA caused degradation of Hdac2 protein in MEFs (FIG. 14A). Expression of miR302/367 did not affect is the levels of Hdac1, 2, or 3 in the presence or absence of VPA in MEFs (FIG. 14A). In contrast, human foreskin fibroblasts expressed much lower levels of Hdac2 protein and the protein levels of Hdac2 were not affected by VPA in these cells (FIG. 14B). These data show that low levels of Hdac2 may significantly enhance or even be required for miR302/367 reprogramming and that human fibroblasts express much lower levels of Hdac2 than MEFs.

Figure 19:
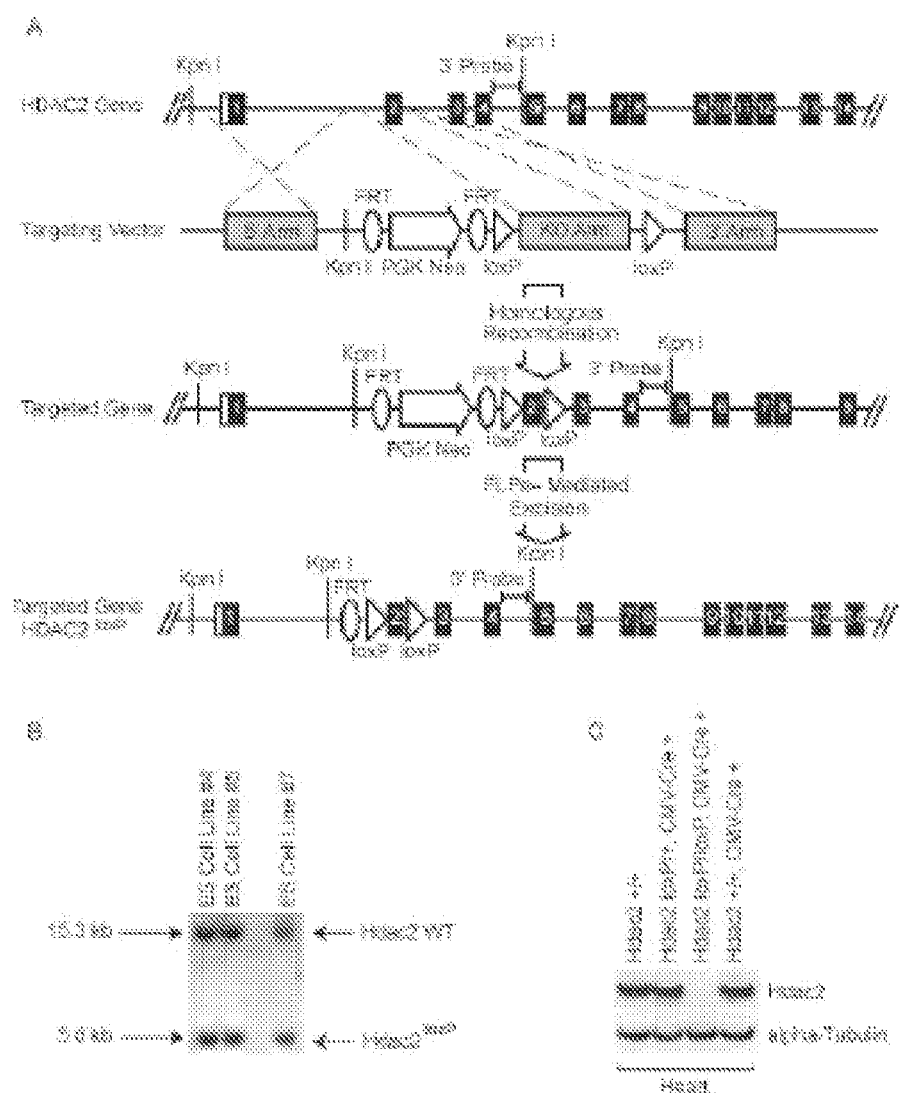
FIG. 19. Generation of conditional Hdac2$^{flox/flox}$ allele. (A) Targeting construct to generate conditional Hdac2$^{flox/flox}$. LoxP sites were introduced upstream and downstream of is exon 2. (B) Southern blot confirming proper targeting in 3 ES clones for the floxed Hdac2 allele. (C) Western blot analysis demonstrating complete deletion of Hdac2 in PO HdacZ$^{flox/flox}$:CMV-cre hearts. Alpha-tubulin expression was used as a loading control.
Figure 20:
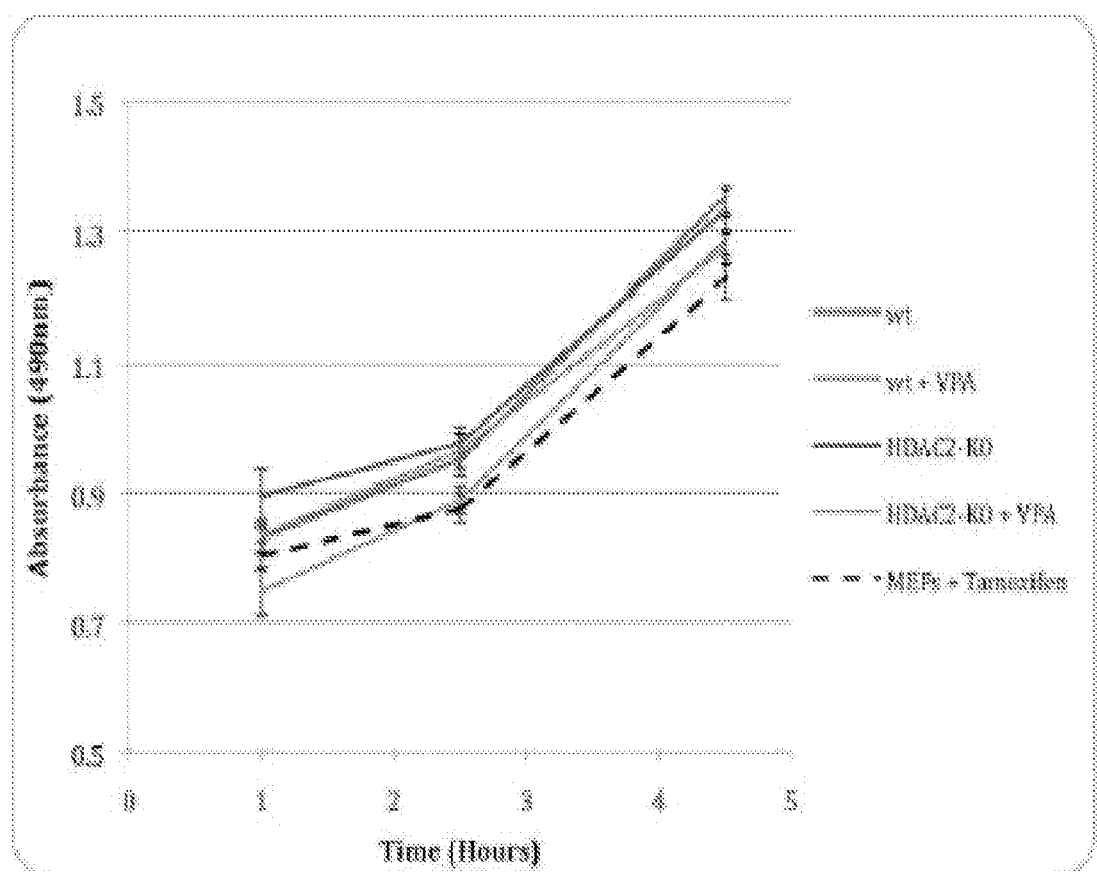
FIG. 20. Cell proliferation of MEFs is not affected by loss of Hdac2 expression or VPA. Cell titer proliferation assays were performed on wild-type (Oct4-GFP) and Hdac2-/- MEFs in the presence or absence of VPA. Cell proliferation changes were measured as noted in the Methods section.

To test whether suppression of Hdac2 is specifically required for efficient reprogramming by miR302/367, we generated Hdac2−/− MEFs from Hdac2$^{flox/flox}$ mice using adenoviral mediated cre excision of Hdac2 and determined whether loss of Hdac2 altered the efficiency of miR302/367 reprogramming of MEFs in the absence of VPA (FIG. 19). We found that in Hdac2−/− MEFs transduced with the miR302/367 virus, Oct4-GFP positive clones were observed as early as six days post-viral infection (FIG. 14C). Eight days after viral transduction, Hdac2−/− MEFs had formed significant numbers of iPS cell clones in the absence of VPA whereas wild-type MEFs in the absence of VPA did not generate any viable clones (FIG. 14D). VPA addition to Hdac2−/− MEFs did not change the number of iPS cell clones obtained (FIG. 14D). The number of iPS cell clones generated and the percentage of clones that were Oct4-GFP positive with miR302/367 transduced wild-type MEFs plus VPA and miR302/367 transduced Hdac2−/− MEFs lacking VPA were similar (FIGS. 14D and E). Loss of Hdac2 expression or VPA addition did not affect proliferation rates in MEFs (FIG. 20). Q-PCR to assess expression of pluripotency related genes also shows increased reprogramming by miR302/367 in Hdac2−/− MEFs compared to wild-type MEFs without VPA (FIG. 14F). Thus, low levels of Hdac2 or suppression of Hdac2 is required for efficient pluripotent stem cell reprogramming by miR302/367.

Current strategies for generating iPS cells rely upon expression of multiple pluripotent stem cell associated transcription factors. We show that a single miRNA cluster, miR302/367, can reprogram fibroblasts more efficiently than the standard OSKM method. With ongoing advances in miRNA biology, these findings may lead to a non-viral, non-transcription factor mediated procedure for generating iPS cells for use not only in basic stem cell biology studies but also for high throughput generation of human iPS clones from large patient populations.

At this point the low efficiency of iPS reprogramming is an impediment to adapting the process to high throughput approaches. Such approaches would allow for the generation of iPS clones from large patient populations obtained from genome wide association studies for use in characterizing the identified genomic differences at the cell biological level. Our is finding that reprogramming by miR302/367 is up to two orders of magnitude more efficient than the OSKM factors indicate that this method may prove to be amenable for use in large scale iPS cell generation. Several other reports have demonstrated that using techniques including Sendai viral expression as well as direct transfection of synthesized mRNAs for the OSKM factors can improve upon the efficiency of iPS reprogramming (Seki et al., 2010; Warren et al., 2010). Based on our data, we obtain efficiencies that are greater than either of these techniques and using human fibroblasts the percent of cells that generate iPS cell clones approaches 10%. Thus, miR302/367 iPS cell reprogramming is more efficient than previously described methods including transfection of synthetic mRNAs for OSKM factors.

The mechanism underlying the increased efficiency of miR302/367 iPS reprogramming is likely to revolve in part around the nature of miRNA biology. First, miRNA expression does not require protein translation and thus leads to a fast response in protein expression based on inhibition of mRNA translation and stability. Second, miRNAs generally target scores or hundreds of mRNAs that coordinate expression of many different proteins which can rapidly impose a dominant phenotypic change in cell identity. This ability to target many different mRNAs simultaneously also increases the complexity underlying the mechanism of miR302/367 function. miR302/367 collectively targets hundreds of different mRNA targets including those that regulate chromatin remodeling and cell proliferation based on bioinformatic prediction algorithms. Our data show that miR367 expression is essential for iPS cell reprogramming by the miR302/367 cluster. As miR367 has a different seed sequence suggesting a different set of mRNA targets, analysis of the combinatorial regulation of miR302a/b/c/d and miR367 targets may provide important information regarding both the pluripotent gene network and also factors whose expression is required to be suppressed for efficient iPS cell reprogramming.

Our studies underscore the role of Hdac2 in iPS cell reprogramming. The specific degradation of Hdac2 protein by VPA is likely the reason that this small molecule has been found to be more efficacious than other Hdac enzymatic inhibitors in enhancing iPS reprogramming. Hdac2 has also been found to be part of an extended regulatory network for to pluripotency in ES cells by interacting with both Oct4 and Myc. Since iPS cell reprogramming involves the resetting of the epigenetic state of a differentiated cell to a pluripotent "ground state", additional studies into the necessity of chromatin remodeling will likely lead to better insight into cell lineage trans-differentiation events. Our finding that human cells, which express much lower levels of Hdac2 protein, do not require VPA for miR302/367 mediated reprogramming indicates that differing levels of Hdac2 may account, at least in part, for the different iPS cell reprogramming efficiencies exhibited by different cell lineages. Moreover, Hdac2 expression may decline during development such that adult cells have little Hdac2 protein resulting in an absence of an affect by VPA.

Our studies clearly show that miRNAs can be powerful tools for mediating iPS cell reprogramming without the need for pluripotent factors including the OSKM factors.

Example 8

Single Transfection of Mimecs Initiate the Pluripotent Repramming Process

Figure 21:
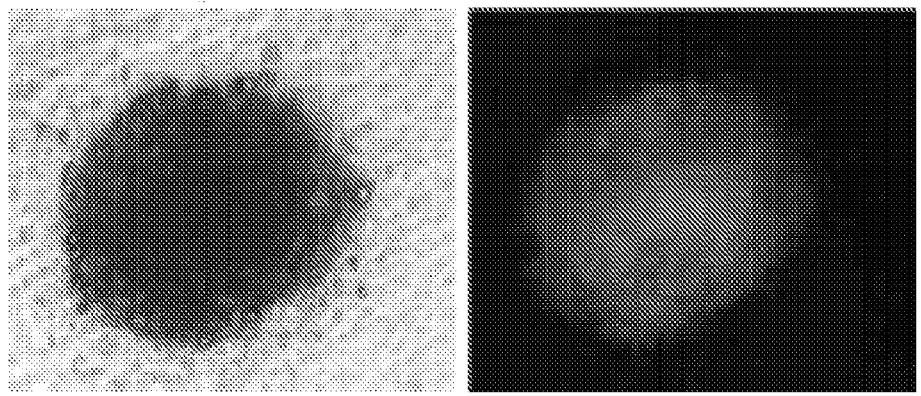
FIG. 21: miR302/367 mimics are sufficient to induce iPS cells. Oct4-GFP KI primary E13.5 MEFs were transfected with mimics for miR302a-d and 367.

Our data show that transfection of miR302/367 mimics can initiate the pluripotent reprogramming process (FIG. 21). Oct4-GFP MEFs were transfected with mimics for miR302a, 302b, 302c, 302d, and 367 and nine days later GFP positive colonies were found (FIG. 21). This is a single transfection and as such is much less laborious than previous reports using multiple transfection of mRNAs for OSKM factors. This procedure can be optimized by altering the concentration of mimics, determining which mimics are essential for the reprogramming process (the miR302 family all have the same seed sequence so all may not be needed), and whether transfection is even required as cholesterol modified mimics are passively taken up by cells. All resulting reprogrammed clones can be characterized as we have for the viral induced miR302/367 clones and OSKM clones.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of inducing the formation of an induced pluripotential stem (iPS) cell from a non-cancerous somatic cell, the method comprising contacting said somatic cell with a composition comprising a) an isolated nucleic acid comprising a microRNA (miR) 302-367 cluster or a miR 302-367 cluster mimic and b) valproic acid, wherein said composition enhances the induction of the formation of said iPS cell from said non-cancerous somatic cell, wherein formation of said iPS cell is induced from said somatic cell without transducing said somatic cell with a nucleic acid that expresses one or more of Oct3/4, Klf4, Sox2 or c-Myc genes.

2. The method of claim 1, wherein said miR is operably linked to a regulatory sequence.

3. The method of claim 2, wherein said regulatory sequence is a constitutive promoter.

4. The method of claim 2, wherein said regulatory sequence is an inducible promoter.

5. The method of claim 4, wherein said inducible promoter is a doxycycline inducible promoter.

6. The method of claim 1, wherein said miR is a miR 302-367 cluster mimic.

7. The method of claim 1, wherein the nucleic acid sequence encoding said miR is present within a vector.

8. The method of claim 7, wherein said vector is a viral vector.

9. The method of claim 8, wherein said viral vector is a lentivirus vector.

10. The method of claim 7, wherein said vector is a plasmid vector.

11. The method of claim 1, wherein said somatic cell is a fibroblast cell.

12. The method of claim 1, wherein said fibroblast cell is an embryonic fibroblast cell.

13. The method of claim 1, wherein said valproic acid is present in a concentration of 2 mM.

14. The method of claim 1, wherein the efficiency of said iPS cell formation is at least 10%.

15. A method of increasing the efficiency of nuclear reprogramming of a somatic cell, comprising contacting said somatic cell with a composition comprising a) an isolated nucleic acid comprising a microRNA (miR) 302-367 cluster and b) valproic acid, without transducing said somatic cell with a nucleic acid that expresses one or more of Oct3/4, Klf4, Sox2, or c-Myc genes.

16. A method of enhancing the induction of the formation of an induced pluripotential stem (iPS) cell from a non-cancerous somatic cell, the method comprising contacting said somatic cell with a composition comprising a) an isolated nucleic acid comprising one or more mimics or one or more pre-miRNA precursors associated with a miR 302-367 and b) valproic acid, wherein said composition enhances the induction of the formation of said iPS cell from said non-cancerous somatic cell, wherein formation of said iPS cell is induced from said somatic cell without transducing said somatic cell with a nucleic acid that expresses one or more of Oct3/4, Klf4, Sox2 or c-Myc genes.

* * * * *

UNITED STATES PATENT AND TRADEMARK OFFICE
CERTIFICATE OF CORRECTION

| | | |
|---|---|---|
| PATENT NO. | : 9,115,345 B2 | Page 1 of 1 |
| APPLICATION NO. | : 13/641521 | |
| DATED | : August 25, 2015 | |
| INVENTOR(S) | : Edward E. Morrisey | |

It is certified that error appears in the above-identified patent and that said Letters Patent is hereby corrected as shown below:

In the Specification

Please replace lines 17-20, in column 1, with the following:

This invention was made with government support under grant number HL087825 and HL100405 awarded by the National Institute of Health. The government has certain rights in the invention.

Signed and Sealed this
Thirty-first Day of May, 2016

Michelle K. Lee
*Director of the United States Patent and Trademark Office*